United States Patent
Teulon et al.

(10) Patent No.: US 9,458,239 B2
(45) Date of Patent: *Oct. 4, 2016

(54) MONOCLONAL ANTIBODIES AND FRAGMENT THEREOF DIRECTED AGAINST THE HUMAN ANTI-MULLERIAN HORMONE TYPE II RECEPTOR (AMHR-II)

(75) Inventors: Isabelle Teulon, Saint Gely du Fesc (FR); André Pelegrin, Montpellier (FR)

(73) Assignee: INSTITUT NATIONAL DE LA SANTE ET DE LA RECHERCHE MEDICALE (INSERM), Paris (FR)

( * ) Notice: Subject to any disclaimer, the term of this patent is extended or adjusted under 35 U.S.C. 154(b) by 36 days.

This patent is subject to a terminal disclaimer.

(21) Appl. No.: 13/604,200

(22) Filed: Sep. 5, 2012

(65) Prior Publication Data

US 2013/0164300 A1    Jun. 27, 2013

Related U.S. Application Data

(62) Division of application No. 12/513,248, filed as application No. PCT/IB2007/003301 on Oct. 31, 2007, now Pat. No. 8,278,423.

(30) Foreign Application Priority Data

Nov. 2, 2006 (EP) .................................. 06291703

(51) Int. Cl.
| | |
|---|---|
| *A61K 39/00* | (2006.01) |
| *C07K 16/28* | (2006.01) |
| *G01N 33/53* | (2006.01) |
| *G01N 33/50* | (2006.01) |

(52) U.S. Cl.
CPC ............ *C07K 16/2869* (2013.01); *C07K 16/28* (2013.01); *A61K 2039/505* (2013.01); *C07K 2317/56* (2013.01); *C07K 2317/565* (2013.01); *C07K 2317/73* (2013.01); *G01N 33/50* (2013.01)

(58) Field of Classification Search
None
See application file for complete search history.

(56) References Cited

U.S. PATENT DOCUMENTS 8,278,423 B2 * 10/2012 Teulon et al. .............. 530/388.1
2004/0229301 A1    11/2004 Wang

OTHER PUBLICATIONS

Paul, W.E. Fundamental Immunology, Third Edition (textbook), "Fv Structure and Diversity in Three Dimensions" pp. 292-295; Raven Press, New York (1993).*
Casset et al. A peptide mimetic of an anti-CD4 monoclonal antibody by rational design. Biochem Biophys Res Comm. vol. 307:198-205 (2003).*
De Pascalis et al. Grafting of "abbreviated" complementarity-determining regions containing specificity-determinig residues essential for ligand contact to engineer a less immunogenic humanized monoclonal antibody. The Journal of Immunology, 169:3076-3084, (2002).*
Rudikoff et al. Single amino acid substitution altering antigen-binding specificity. Proc. Natl. Acad. Sci. USA, 79(6):1979-1983 (Mar. 1982).*
Bendig M. M. Humanization of rodent monoclonal antibodies by CDR grafting. Methods: A Companion to Methods in Enzymology, vol. 8:83-93 (1995).*
Salhi et al. The anti-Mullerian hormone type II receptor: insights into the binding domains recognized by a monoclonal antibody and the natural ligand. Biochem. J. vol. 379, 785-793 (2004).*

* cited by examiner

*Primary Examiner* — Elizabeth C Kemmerer
*Assistant Examiner* — Regina M Deberry
(74) *Attorney, Agent, or Firm* — B. Aaron Schulman, Esq.; Stites & Harbison, PLLC

(57) ABSTRACT

The present invention relates to monoclonal antibodies and fragment thereof directed against the human Anti-Müllerian Hormone type II receptor (AMHR-II) and their use for treating and diagnosing cancer diseases, such as ovarian cancers.

19 Claims, 6 Drawing Sheets

FIG.3 clone 12G4 anti-AMHR-II
AA

```
                        1                FR1 VH                    11                          15                                      20  21
                        CAG GTC CAG CTG CAG CAG TCT GGA CCT GAA CTG GTG AAG CCT GGG GCT TCA GTG AGG ATG TCC TGC AAG
                         Q   V   Q   L   Q   Q   S   G   P   E   L   V   K   P   G   A   S   V   R   M   S   C   K
                                                                              CDR1 VH
                         25      27                                    30                              34
                        GCT TCT GGA TAC ACC TTC ACA AGT TAC CAT ATA CAC TGG GTG AAG CAG AGG CCT GGA CAG GGA CTT GAG
                         A   S   G   Y   T   F   T   S   Y   H   I   H   W   V   K   Q   R   P   G   Q   G   L   E
                                                                              FR2 VH                       45                           50
                                              CDR2 VH
                                        55                                                       63
                        TGG ATT GGA ATT TAT CCT GGC GAT GAT TCT ACT AAA TAC AAT GAG AAG TTC AAG GGC AAG ACC ACA
                         W   I   G   I   Y   P   G   D   D   S   T   K   Y   N   E   K   F   K   G   K   T   T
                         69                                    FR3 VH                                            75
                         80                                                                          90
                        CTG ACT GCA GAC AAA TCC TCC AGC ACA GCC TAC ATG TTG CTC AGC AGC CTG ACC TCT GAG GAC TCT GCA GCC
                         L   T   A   D   K   S   S   S   T   A   Y   M   L   L   S   S   L   T   S   E   D   S   A
                                                                              FR3 VH                95              100
                                                               CDR3 VH
                         104 105                                   110
                        ATC TAT TTC TGT ACA AGG GGG GAC CGG TTT GCT TAC TGG GGC CAA GGG ACT CTG GTC ACT GTC TCT GCA GCC AAA ACG ACA CCC
                         I   Y   F   C   T   R   G   D   R   F   A   Y   W   G   Q   G   T   L   V   T   V   S   A
                                           D - J                               FR4 VH               115               120
```

MONOCLONAL ANTIBODIES AND FRAGMENT THEREOF DIRECTED AGAINST THE HUMAN ANTI-MULLERIAN HORMONE TYPE II RECEPTOR (AMHR-II)

This application is a divisional application of U.S. application Ser. No. 12/513,248 having a filing date of Jan. 22, 2010, which was a National Stage of International Application No.: PCT/IB2007/003301, filed Oct. 31, 2007, all of said applications incorporated herein by reference.

The present invention relates to monoclonal antibodies and fragment thereof directed against the human Anti-Müllerian Hormone type II receptor (AMHR-II) and their use for treating and diagnosing cancer diseases, such as ovarian cancers.

Ovarian cancer is the leading cause of gynaecological malignancy and is the fifth most common cause of cancer-related death in women. With an average incidence of about 10 per 100 000, a total of 1-2% of all European women present an ovarian cancer at some point in their lives (Black R J et al. 1997).

Granulosa cell tumours (GCT) account for about 5% of malignant neoplasms of the ovary and for 70% of the ovarian sex cord-stromal tumours. Although their malignant potential is relatively low in the first years of the disease, recurrences may appear up to 30 years after surgical removal of primary tumours (Singh-Ranger G et al. 2004). If the diagnosis is made early, before tumour has spread over the peritoneum, prognosis of recurrences can be significantly improved by complete surgical removal (Dutertre M. et al., 2001).

Epithelial ovarian cancers represent about 80% of all ovarian tumours. When these carcinomas are diagnosed at early stages, the survival rate is about 90%. Unfortunately, at diagnosis, approximately 75% of women have already widespread intra-abdominal disease dissemination (American Cancer Society Facts and Figures. 2001 www.cancer.org). In those cares, the survival rate is about 20-25% despite appropriate treatment (Rapkiewicz A V. et al. 2004).

Some molecular markers were proposed for epithelial ovarian cancer, especially the circulating form of cancer antigen 125 (CA125 or MUC16) which is over expressed in about 80% of these tumours. However the elevation of its level may be associated with menstruation and benign conditions such as endometriosis or liver disease.

The main therapeutic strategies used for epithelial ovarian cancer are surgery and chemotherapy. For example, ovarian cancer has generally been treated with cisplatin-based chemotherapy but often recurs due to acquired cisplatin resistance (Yahata, H. et al., 2002). Although most patients may initially respond to platinium and paclitaxel chemotherapy, including complete responses, the relapse rate is approximately 85% (Gordon A N et al. 2004). New targeted therapies based on hormones, anti-angiogenic factors and monoclonal antibody have rapidly developed. Monoclonal antibodies include oregovomab (OvaRex, AltaRex), an investigational murine monoclonal antibody directed against CA125, currently used in clinical trials as an immunotherapeutic treatment (Berek J S et al. 2004), and cetuximab, which is directed against the epidermal growth factor receptor (EGFR), expressed in 30 to 70% of epithelial ovarian cancers (Ozols R F et al. 2004).

Thus, important needs exist for new therapeutic agents for the treatment of ovarian cancer. Additionally, there is a clear need to identify new ovarian cancer-associated proteins for use as sensitive and specific biomarkers for the diagnosis of ovarian cancer in living subjects.

The anti-Müllerian Hormone type II receptor is involved in Müllerian duct regression associated with the development of the male reproductive system. This receptor is frequently expressed on human epithelial ovarian tumour cells. As the capability of AMH to inhibit the growth of ovarian cancer cells has been demonstrated, AMHR-II could thus constitute a valuable target for antibody-based immunotherapy.

AMHR-II expression has been studied in animal models by genetic manipulation of the mouse germ line. Dutertre et al. (2001) reported the expression of a functional AMHR-II in granulosa cell ovarian tumours derived from transgenic mice obtained by targeted oncogenesis using an AMH promoter SV40 oncogene construct. In a recently developed mouse model, Conolly et al. (2003) using a construct of the same oncogene under the control of the AMHR-II 5' upstream regulatory sequence, demonstrated that about 50% of female mice developed epithelial ovarian. Masiakos et al. (1999) also demonstrated the expression of AMHR-II in human epithelial ovarian cancer cell lines, samples of ascite cells isolated from patients and solid tumours form patients with ovarian carcinoma. These investigators also reported the expression of AMHR-II in cancer cell lines derived from other tissues such as breast (Segev D L et al; 2000) or prostate (Segev D L et al. 2002). These data suggest a very specific profile of AMHR-II in human cancers, especially in ovarian tumours.

In 2004, Salhi et al. developed and characterized a monoclonal antibody (mAb) directed against the human AMHR-II, and demonstrated by immunohistochemistry (IHC) the strong expression of AMHR-II by human granulosa cell tumours (GCTs) and by Sertoli and Leydig cells on human testis. They also clearly showed the non-competitive binding of mAb 12G4 in Granulosa Cell Tumours expressing a high level of the natural ligand (AMH) thus allowing the in vivo use of mAb 12G4 in AMHR-II expressing tumours.

More recently, Yuan et al. (2006) described the selection of AMHR-II specific human scFv (single chain variable fragments) molecules from a human non immune scFv phage-displayed library. They further suggested that antibody-based constructs may provide a highly specific means of targeting AMHR-II on human ovarian carcinoma cells for the purpose of diagnosing and treating this disease.

The present invention gives a publicly available source of the specific monoclonal antibody developed by Salhi et al. (2004), which is referred by the inventors as mAb 12G4. Indeed, a mAb 12G4 producing hybridoma has been deposited at the Collection Nationale de Cultures de Microorganismes (CNCM, Institut Pasteur, 25 rue du Docteur Roux, 75724 Paris Cedex 15, France), in accordance with the terms of Budapest Treaty, on the 26 Sep. 2006. The deposited hybridoma has CNCM deposit number I-3673. The inventors have also cloned and characterized the variable domain of the light and heavy chains of said mAb 12G4, and thus determined the complementarity determining regions (CDRs) of said antibody.

Furthermore, the inventors have investigated by immunohistochemistry using the mAb 12G4, the expression of AMHR-II in tissue sections from various tumours. They have therefore demonstrated the specific expression profile of AMHR-II in ovarian cancers, not only in epithelial ovarian cancers but also in special subtypes such as serous and clear adenocarcinoma and adult granulosa cell tumours, belonging respectively to malignant epithelial proliferations and to sex cord-stromal tumours. They thus showed that AMHR-II could represent a new diagnostic marker for ovarian AMHR-II positive cancers and could be used as a target for immunotherapy using mAb 12G4 or derivatives thereof.

The inventors recently demonstrated by Immunofluorescence experiments that the mAb 12G4 shows efficient internalization in AMHR-II stably transfected GCT cell line (COV434-pIRES-EGFP-AMHR-II) (Zhang H et al. 2000). This cell line expresses about $10^4$ receptors/cell. They have also shown the in vitro capability of this antibody to inhibit the growth of AMHR-II expressing COV434 cells. In vivo experiments were also performed showing that mAb 12G4 is able to delay tumour growth in a model of athymic nude mice xenografted with COV434-pIRESEGFP-AMHR-II cells.

A first aspect of the invention thus relates to an immunoglobulin heavy and/or light chain wherein the variable domain comprises at least a CDR having a sequence selected from the group consisting of SEQ ID NO:2 or SEQ ID NO:6 for CDR-1, SEQ ID NO:3 or SEQ ID NO:7 for CDR-2 and SEQ ID NO:4 or SEQ ID NO:8 for CDR-3.

A second aspect of the invention relates to a monoclonal antibody or a fragment thereof directed against the Anti-Müllerian Hormone type II receptor (AMHR-II) comprising:
  a heavy chain wherein the variable domain comprises at least a CDR having a sequence selected from the group consisting of SEQ ID NO:2 for CDR-H1, sequence SEQ ID NO:3 for CDR-H2 and sequence SEQ ID NO:4 for CDR-1-13; and/or
  a light chain wherein the variable domain comprises at least a CDR having a sequence selected from the group consisting of SEQ ID NO:6 for CDR-L1, sequence SEQ ID NO:7 for CDR-L2 region and sequence SEQ ID NO:8 for CDR-L3.

A third aspect of the invention relates to a nucleic acid comprising a sequence encoding a monoclonal antibody or fragment thereof according to the invention.

A fourth aspect of the invention relates to a vector comprising a nucleic acid according to the invention.

A fifth aspect of the invention relates to a host cell, which has been transformed by a nucleic acid and/or a vector as above described.

A sixth aspect of the invention relates to a method of producing an antibody according to the invention, which method comprises the steps consisting of: (i) culturing a transformed host cell as above described under conditions suitable to allow expression of said antibody; and (ii) recovering the expressed antibody.

A seventh aspect of the invention relates to a pharmaceutical composition comprising an antibody, and/or nucleic acid, and/or a vector, and/or a host cell as above described together with a pharmaceutically acceptable carrier.

An eighth aspect of the invention relates to an immunoconjugate comprising an antibody according to the invention conjugated to an anti-cancer agent or a growth inhibitory agent.

A ninth aspect of the invention relates to an antibody according the invention which is labelled with a detectable molecule or substance.

A tenth aspect of the invention relates to the use of an antibody, or pharmaceutical composition or an immunoconjugate as above described for the manufacture of a medicament intended for treating an ovarian cancer.

An eleventh aspect of the invention relates to the use of an antibody according to the invention diagnosing and/or monitoring ovarian cancers.

DEFINITIONS

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

As used herein, references to specific proteins (e.g., antibodies or AMHR-II) can include a polypeptide having a native amino acid sequence, as well as variants and modified forms regardless of their origin or mode of preparation. A protein which has a native amino acid sequence is a protein having the same amino acid sequence as obtained from nature (e.g., a naturally occurring AMHR-II). Such native sequence proteins can be isolated from nature or can be prepared using standard recombinant and/or synthetic methods. Native sequence proteins specifically encompass naturally occurring truncated or soluble forms, naturally occurring variant forms (e.g., alternatively spliced forms), naturally occurring allelic variants and forms including post-translational modifications. A native sequence protein includes proteins following post-translational modifications such as glycosylation, or phosphorylation, or other modifications of some amino acid residues.

The term "gene" means a DNA sequence that codes for, or corresponds to, a particular sequence of amino acids which comprises all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription. In particular, the term gene may be intended for the genomic sequence encoding a protein, i.e. a sequence comprising regulator, promoter, intron and exon sequences.

As used herein, the term "oligonucleotide" refers to a nucleic acid, generally of at least 10, preferably at least 12, more preferably at least 15, and still preferably at least 20 nucleotides, preferably no more than 100 nucleotides, still preferably no more than 70 nucleotides.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, more preferably at least 85%, still preferably at least 90%, and even more preferably at least 95%, and which has the same or substantially similar properties or functions as the native or parent protein to which it is compared.

Two amino acid sequences are "substantially homologous" or "substantially similar" when greater than 80%, preferably greater than 85%, preferably greater than 90% of the amino acids are identical, or greater than about 90%, preferably grater than 95%, are similar (functionally identical) over the whole length of the shorter sequence. Preferably, the similar or homologous sequences are identified by alignment using, for example, the GCG (Genetics Computer Group, Program Manual for the GCG Package, Version 7, Madison, Wis.) pileup program, or any of sequence comparison algorithms such as BLAST, FASTA, etc.

According to the present invention, "antibody" or "immunoglobulin" have the same meaning, and will be used equally in the present invention. Antibody refers to immunoglobulin molecules and immunologically active portions of immunoglobulin molecules, i.e., molecules that contain an antigen binding site that immunospecifically binds an antigen. As such, the term antibody encompasses not only whole antibody molecules, but also antibody fragments as well as variants (including derivatives) of antibodies and antibody fragments. In natural antibodies, two heavy chains are linked to each other by disulfide bonds and each heavy chain is linked to a light chain by a disulfide bond. There are two types of light chain, lambda (l) and kappa (k). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, transplacental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, includes six CDRs, comprising the CDR set from each of a heavy and a light chain V region.

Framework Regions (FRs) refer to amino acid sequences interposed between CDRs, i.e. to those portions of immunoglobulin light and heavy chain variable regions that are relatively conserved among different immunoglobulins in a single species, as defined by Kabat, et al (Sequences of Proteins of Immunological Interest (National Institutes of Health, Bethesda, Md., 1991). As used herein, a "human framework region" is a framework region that is substantially identical (about 85%, or more, in particular 90%, 95%, or 100%) to the framework region of a naturally occurring human antibody.

The term "monoclonal antibody" or "mAb" as used herein refers to an antibody molecule of a single amino acid composition, that is directed against a specific antigen and that is produced by a single clone of B cells or hybridoma.

The term "chimeric antibody" refers to an engineered antibody which comprises a VH domain and a VL domain of an antibody derived from a non-human animal, a CH domain and a CL domain of another antibody, in particular a human antibody. As the non-human animal, any animal such as mouse, rat, hamster, rabbit or the like can be used.

The term "humanized antibody" refers to antibodies in which the framework or "complementarity determining regions" (CDR) have been modified to comprise the CDR from a donor immunoglobulin of different specificity as compared to that of the parent immunoglobulin. In a preferred embodiment, a mouse CDR is grafted into the framework region of a human antibody to prepare the "humanized antibody".

"Antibody fragments" comprise a portion of an intact antibody, preferably the antigen binding or variable region of the intact antibody. Examples of antibody fragments include Fv, Fab, F(ab')2, Fab', dsFv, scFv, sc(Fv)2, diabodies and multispecific antibodies formed from antibody fragments. The term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond.

The term "F(ab')2" refers to an antibody fragment having a molecular weight of about 100,000 and antigen binding activity, which is slightly larger than the Fab bound via a disulfide bond of the hinge region, among fragments obtained by treating IgG with a protease, pepsin.

The term "Fab'" refers to an antibody fragment having a molecular weight of about 50,000 and antigen binding activity, which is obtained by cutting a disulfide bond of the hinge region of the F(ab')2.

A single chain Fv ("scFv") polypeptide is a covalently linked VH::VL heterodimer which is usually expressed from a gene fusion including VH and VL encoding genes linked by a peptide-encoding linker. The human scFv fragment of the invention includes CDRs that are held in appropriate conformation, preferably by using gene recombination techniques.

"dsFv" is a VH::VL heterodimer stabilised by a disulphide bond. Divalent and multivalent antibody fragments can form either spontaneously by association of monovalent scFvs, or can be generated by coupling monovalent scFvs by a peptide linker, such as divalent sc(Fv)$_2$.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

The term "hybridoma" denotes a cell, which is obtained by subjecting a B cell prepared by immunizing a non-human mammal with an antigen to cell fusion with a myeloma cell derived from a mouse or the like which produces a desired monoclonal antibody having an antigen specificity.

The term "AMHR-II" denotes the Anti-Müllerian Hormone type II Receptor. The AMHR-II gene has been isolated in the rat (Baarends W M et al. 1994), rabbit (di Clemente N. et al. 1994), human (hAMHR-II) (Imbeaud S et al. 1995)

and mouse (mAMHR-II) (Behringer R R et al. 1990). It contains 11 exons: exons 1-3 code for the extracellular domain, composed of 127 amino acids in the human receptor, and exon 4 codes for the transmembrane domain, composed of 26 amino acids. The predicted sequence of AMHR-II shares an overall similarity of approximately 30% with other type II receptors of the TGF-β family. AMHR-II is specifically expressed in the natural tissue targets, the reproductive organs and the gonads. In the Müllerian duct, where AMH (Anti-Müllerian Hormone) induces regression by a paracrine mechanism, AMHR-II is expressed in the mesenchyme (Tsuji M et al. 1992). Mutations in AMHR-II or AMH cause male sexual abnormalities, e.g. pseudohermaphroditism in male transgenic mice (Behringer R R et al. 1990) (known as persistent Müllerian duct syndrome (PMDS) in humans (Belville C et al. 1999)). In the female, AMHR-II expression is maintained along the length of the Müllerian duct, and is detected in the normal and gravid uterus (Teixeira J et al. 1996). Female AMHR-II- or AMH-deficient mice are normal and as fertile as young adults. AMH and AMHR-II are co-expressed in the testicular Sertoli and ovarian granulosa cells, and in derived cells, such as Smat-1 (Dutertre M et al. 1997) and AT29C (Racine C et al. 1998), respectively. Expression of AMHR-II alone has been detected in Leydig cells of rodents (Racine C, et al. 1998; Lee M M et al. 1999) and in cells of humans (Masiakos P T et al. 1999), but not in murine ovarian surface epithelium (di Clemente et al. 1994; Baarends W M et al. 1995). The polypeptide sequence of human AMHR-II is deposited in Genebank database under accession number U29700.

By "purified" and "isolated" it is meant, when referring to a polypeptide (i.e. the antibody fragment of the invention) or a nucleotide sequence, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type are present. An "isolated" nucleic acid molecule which encodes a particular polypeptide refers to a nucleic acid molecule which is substantially free of other nucleic acid molecules that do not encode the subject polypeptide; however, the molecule may include some additional bases or moieties which do not deleteriously affect the basic characteristics of the composition.

As used herein, the term "subject" denotes a mammal, such as a rodent, a feline, a canine, and a primate. Preferably a subject according to the invention is a human.

Antibodies, Immunoglobulin Chains and Polypeptides of the Invention:

The present invention provides for isolated monoclonal antibodies or fragments thereof that are directed against human AMHR-II. In particular, the inventors have deposited the mAb 12G4 producing hybridoma at the Collection Nationale de Cultures de Microorganismes (CNCM, Institut Pasteur, 25 rue du Docteur Roux, 75724 Paris Cedex 15, France), in accordance with the terms of Budapest Treaty, on the 26 Sep. 2006. The deposited hybridoma has CNCM deposit number I-3673. The inventors have cloned and characterized the variable domain of the light and heavy chains of said mAb 12G4, and thus determined the complementarity determining regions (CDRs) domain of said antibody as described in Table 1 and FIGS. 2 and 3:

TABLE 1

VH, VL and CDR domains of mAb12G4:

| MAb 12G4 Domains | Sequence |
|---|---|
| VH | QVQLQ QSGPE LVKPG ASVRM SCKAS GYTFT SYHIH WVKQR PGQGL EWIGW IYPGD DSTKY NEKFK GKTTL TADKS SSTAY MLLSS LTSED SAIYF CTRGD RFAYW GQGTL VTVSA (SEQ ID NO: 1) |
| VH CDR1 | GYTFT SYH (SEQ ID NO: 2) |
| VH CDR2 | IYPGD DST (SEQ ID NO: 3) |
| VH CDR3 | TRGD R FAY (SEQ ID NO: 4) |
| VL | QIVLT QSPAI MSASL GEGIT LTCSA SSSVR YIHWY QQKSG TSPKL LIYST SNLAS GVPSR FSGSG SGTFH SLTISS VEAED AADYY CLQWS SYPWT FGGGT KLEIK (SEQ ID NO: 5) |
| VL CDR1 | SSVRY (SEQ ID NO: 6) |
| VL CDR2 | STS (SEQ ID NO: 7) |
| VL CDR3 | LQWSS YPWT (SEQ ID NO: 8) |

Therefore, the invention relates to a monoclonal antibody having specificity for human AMHR-II, comprising a heavy chain wherein the variable domain comprises at least a CDR having a sequence selected from the group consisting of SEQ ID NO:2 for CDR-H1, SEQ ID NO:3 for CDR-H2 and SEQ ID NO:4 for CDR-H3.

The invention also relates to a monoclonal antibody having specificity for human AMHR-II, comprising a light chain wherein the variable domain comprises at least a CDR having a sequence selected from the group consisting of SEQ ID NO:6 for CDR-L1, SEQ ID NO:7 for CDR-L2 and SEQ ID NO:8 for CDR-L3.

The invention also relates to a monoclonal antibody having specificity for human AMHR-II, comprising a heavy chain wherein the variable domain comprises at least a CDR having a sequence selected from the group consisting of SEQ ID NO:2 or SEQ ID NO:6 for CDR-H1, SEQ ID NO:3 or SEQ ID NO:7 for CDR-H2 and SEQ ID NO:4 or SEQ ID NO:8 for CDR-H3; and/or a light chain wherein the variable domain comprises at least a CDR having a sequence selected from the group consisting of SEQ ID NO:2 or SEQ ID NO:6 for CDR-H1, SEQ ID NO:3 or SEQ ID NO:7 for CDR-H2 and SEQ ID NO:4 or SEQ ID NO:8 for CDR-H3.

The monoclonal antibody of the invention, may comprise a heavy chain wherein the variable domain comprises at least a CDR having a sequence selected from the group consisting of SEQ ID NO:2 for CDR-H1, SEQ ID NO:3 for CDR-H2 and SEQ ID NO:4 for CDR-H3 and/or a light chain wherein the variable domain comprises at least a CDR having a sequence selected from the group consisting of SEQ ID NO:6 for CDR-L1, SEQ ID NO:7 for CDR-L2 and SEQ ID NO:8 for CDR-L3.

The monoclonal antibody of the invention, may comprise a light chain wherein the variable domain comprises at least a CDR having a sequence selected from the group consisting of SEQ ID NO:2 for CDR-H1, SEQ ID NO:3 for CDR-H2 and SEQ ID NO:4 for CDR-H3 and/or a heavy chain wherein the variable domain comprises at least a CDR having a sequence selected from the group consisting of SEQ ID NO:6 for CDR-L1, SEQ ID NO:7 for CDR-L2 and SEQ ID NO:8 for CDR-L3. In particular, the invention provides a monoclonal antibody directed against the Anti-Müllerian Hormone type II receptor (AMHR-II) comprising:

an heavy chain wherein the variable domain comprises
a) SEQ ID NO:2 in the CDR-H1 region, SEQ ID NO:3 in the CDR-H2 region and SEQ ID NO:4 in the CDR-H3 region; or
b) SEQ ID NO:6 in the CDR-H1 region, SEQ ID NO:7 in the CDR-H2 region and SEQ ID NO:8 in the CDR-H3 region;
and/or
a light chain wherein the variable domain comprises
c) SEQ ID NO:6 in the CDR-L1 region, SEQ ID NO:7 in the CDR-L2 region and SEQ ID NO:8 in the CDR-L3 region; or
d) SEQ ID NO:2 in the CDR-L1 region, SEQ ID NO:3 in the CDR-L2 region and SEQ ID NO:4 in the CDR-L3 region.

In a particular embodiment, the heavy chain variable domain of said antibody has the amino acid sequence set forth as SEQ ID NO: 1 or SEQ ID NO:5 and/or the light chain variable domain has the amino acid sequence set forth as SEQ ID NO: 5 or SEQ ID No:1.

Said antibodies can be produced by any technique well known in the art. In particular said antibodies are produced by techniques as hereinafter described.

According to an embodiment, the monoclonal antibody of the invention is a murine antibody. In particular, said murine antibody may be obtainable from the hybridoma available under CNCM deposit number I-3673.

In another embodiment, the monoclonal antibody of the invention is a chimeric antibody, preferably a chimeric mouse/human antibody. In particular, said mouse/human chimeric antibody may comprise the variable domains of an antibody obtainable from hybridoma deposited as CNCM-I-3673.

In another embodiment, the monoclonal of the invention is a humanized antibody. In particular, in said humanized antibody, the variable domain comprises human acceptor frameworks regions, and optionally human constant domain where present, and non-human donor CDRs, such as mouse CDRs as defined above.

The invention further provides fragments of said monoclonal antibodies which include but are not limited to Fv, Fab, F(ab')2, Fab', dsFv, scFv, sc(Fv)2 and diabodies; and multispecific antibodies formed from antibody fragments.

In another aspect, the invention relates to an immunoglobulin heavy and/or light chain wherein the variable domain comprises at least a CDR having a sequence selected from the group consisting of SEQ ID NO:2 or SEQ ID NO:6 for CDR-1, SEQ ID NO:3 or SEQ ID NO:7 for CDR-2 and SEQ ID NO:4 or SEQ ID NO:8 for CDR-3.

In particular, the invention provides an immunoglobulin heavy and/or light chain wherein the variable domain comprises:
at least a CDR having a sequence selected from the group consisting of SEQ ID NO:2 for CDR-1, SEQ ID NO:3 for CDR-2 and SEQ ID NO:4 for CDR-3; or
at least a CDR having a sequence selected from the group consisting of SEQ ID NO:6 for CDR-1, SEQ ID NO:7 for CDR-2 and SEQ ID NO:8 for CDR-3.

In a preferred embodiment, the invention relates to an immunoglobulin heavy and/or light chain, wherein the variable domain comprises:
SEQ ID NO:2 for CDR-1, SEQ ID NO:3 for CDR-2 and SEQ ID NO:4 for CDR-3; or
SEQ ID NO:6 for CDR-1, SEQ ID NO:7 for CDR-2 and SEQ ID NO:8 for CDR-3.

According to an embodiment, an immunoglobulin heavy and/or light chain according to the invention comprises a variable domain having the amino acid sequence set forth as SEQ ID NO:1 or SEQ ID NO:5.

In one embodiment, an immunoglobulin chain according to the invention is a heavy chain or a light chain.

The invention further relates to an immunoglobulin which comprises an immunoglobulin heavy or light chain according to the invention. In particular, the immunoglobulin may comprise heavy or light chains as defined above.

In another aspect, the invention relates to a polypeptide which has a sequence selected from the group consisting of SEQ ID NO: 1, SEQ ID NO:2, SEQ ID NO:3, SEQ ID NO:4, SEQ ID NO:5; SEQ ID NO: 6; SEQ ID NO:7 and SEQ ID NO:8.

Antibodies and polypeptides of the invention can be use in an isolated (e.g., purified) form or contained in a vector, such as a membrane or lipid vesicle (e.g. a liposome).

Nucleic Acids, Vectors and Recombinant Host Cells

A further object of the invention relates to a nucleic acid sequence encoding a monoclonal antibody of the invention or a fragment thereof.

In a particular embodiment, the invention relates to a nucleic acid sequence encoding the VH domain of mAb 12G4 or the VL domain of mAb 12G4.

Typically, said nucleic acid is a DNA or RNA molecule, which may be included in any suitable vector, such as a plasmid, cosmid, episome, artificial chromosome, phage or a viral vector.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence.

So, a further object of the invention relates to a vector comprising a nucleic acid of the invention.

Such vectors may comprise regulatory elements, such as a promoter, enhancer, terminator and the like, to cause or direct expression of said polypeptide upon administration to a subject. Examples of promoters and enhancers used in the expression vector for animal cell include early promoter and enhancer of SV40 (Mizukami T. et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like.

Any expression vector for animal cell can be used, so long as a gene encoding the human antibody C region can be inserted and expressed. Examples of suitable vectors include pAGE107 (Miyaji H et al. 1990), pAGE103 (Mizukami T et al. 1987), pHSG274 (Brady G et al. 1984), pKCR(O'Hare K et al. 1981), pSG1 beta d2-4-(Miyaji H et al. 1990) and the like.

Other examples of plasmids include replicating plasmids comprising an origin of replication, or integrative plasmids, such as for instance pUC, pcDNA, pBR, and the like.

Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. No. 5,882,877, U.S. Pat. No. 6,013,516, U.S. Pat. No. 4,861,719, U.S. Pat. No. 5,278,056 and WO 94/19478.

A further object of the present invention relates to a cell which has been transfected, infected or transformed by a nucleic acid and/or a vector according to the invention.

The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed".

The nucleic acids of the invention may be used to produce a recombinant polypeptide of the invention in a suitable expression system. The term "expression system" means a host cell and compatible vector under suitable conditions, e.g. for the expression of a protein coded for by foreign DNA carried by the vector and introduced to the host cell.

Common expression systems include E. coli host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include E. coli, Kluyveromyces or Saccharomyces yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolate reductase gene (hereinafter referred to as "DHFR gene") is defective (Urlaub G et al; 1980), rat YB2/3HL.P2.G11.16Ag.20 cell (ATCC CRL1662, hereinafter referred to as "YB2/0 cell"), and the like. The YB2/0 cell is preferred, since ADCC activity of chimeric or humanized antibodies is enhanced when expressed in this cell.

The present invention also relates to a method of producing a recombinant host cell expressing an antibody or a polypeptide of the invention according to the invention, said method comprising the steps consisting of (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete said antibody or polypeptide. Such recombinant host cells can be used for the production of antibodies and polypeptides of the invention.

Methods of Producing Antibodies of the Invention

Antibodies and polypeptides of the invention may be produced by any technique known in the art, such as, without limitation, any chemical, biological, genetic or enzymatic technique, either alone or in combination.

Knowing the amino acid sequence of the desired sequence, one skilled in the art can readily produce said antibodies or polypeptides, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions. Alternatively, antibodies and polypeptides of the invention can be synthesized by recombinant DNA techniques as is well-known in the art. For example, these fragments can be obtained as DNA expression products after incorporation of DNA sequences encoding the desired (poly)peptide into expression vectors and introduction of such vectors into suitable eukaryotic or prokaryotic hosts that will express the desired polypeptide, from which they can be later isolated using well-known techniques.

In particular, the invention further relates to a method of producing an antibody or a polypeptide of the invention, which method comprises the steps consisting of: (i) culturing a transformed host cell according to the invention under conditions suitable to allow expression of said antibody or polypeptide; and (ii) recovering the expressed antibody or polypeptide.

Antibodies and polypeptides of the invention are suitably separated from the culture medium by conventional immunoglobulin purification procedures such as, for example, protein A-Sepharose, hydroxylapatite chromatography, gel electrophoresis, dialysis, or affinity chromatography.

In a particular embodiment, the human chimeric antibody of the present invention can be produced by obtaining nucleic sequences encoding VL and VH domains as previously described, constructing a human chimeric antibody expression vector by inserting them into an expression vector for animal cell having genes encoding human antibody CH and human antibody CL, and expressing the coding sequence by introducing the expression vector into an animal cell.

As the CH domain of a human chimeric antibody, it may be any region which belongs to human immunoglobulin, but those of IgG class are suitable and any one of subclasses belonging to IgG class, such as IgG1, IgG2, IgG3 and IgG4, can also be used. Also, as the CL of a human chimeric antibody, it may be any region which belongs to Ig, and those of kappa class or lambda class can be used.

Methods for producing chimeric antibodies involve conventional recombinant DNA and gene transfection techniques are well known in the art (See Morrison S L. et al. (1984) and patent documents U.S. Pat. No. 5,202,238; and U.S. Pat. No. 5,204,244).

The humanized antibody of the present invention may be produced by obtaining nucleic acid sequences encoding CDR domains, as previously described, constructing a humanized antibody expression vector by inserting them into an expression vector for animal cell having genes encoding (i) a heavy chain constant region identical to that of a human antibody and (ii) a light chain constant region identical to that of a human antibody, and expressing the genes by introducing the expression vector into an animal cell.

The humanized antibody expression vector may be either of a type in which a gene encoding an antibody heavy chain and a gene encoding an antibody light chain exists on separate vectors or of a type in which both genes exist on the same vector (tandem type). In respect of easiness of construction of a humanized antibody expression vector, easiness of introduction into animal cells, and balance between the expression levels of antibody H and L chains in animal cells, humanized antibody expression vector of the tandem type is preferred (Shitara K et al. 1994). Examples of tandem type humanized antibody expression vector include pKANTEX93 (WO 97/10354), pEE18 and the like.

Methods for producing humanized antibodies based on conventional recombinant DNA and gene transfection techniques are well known in the art (See, e.g., Riechmann L. et al. 1988; Neuberger M S. et al. 1985). Antibodies can be humanized using a variety of techniques known in the art including, for example, CDR-grafting (EP 239,400; PCT publication WO91/09967; U.S. Pat. Nos. 5,225,539; 5,530, 101; and 5,585,089), veneering or resurfacing (EP 592,106; EP 519,596; Padlan E A (1991); Studnicka G M et al. (1994); Roguska M A. et al. (1994)), and chain shuffling (U.S. Pat. No. 5,565,332). The general recombinant DNA technology for preparation of such antibodies is also known (see European Patent Application EP 125023 and International Patent Application WO 96/02576).

The Fab of the present invention can be obtained by treating an antibody which specifically reacts with human AMHR-II with a protease, papaine. Also, the Fab can be produced by inserting DNA encoding Fab of the antibody into a vector for prokaryotic expression system, or for eukaryotic expression system, and introducing the vector into a procaryote or eucaryote (as appropriate) to express the Fab.

The F(ab')2 of the present invention can be obtained treating an antibody which specifically reacts with AMHR-II with a protease, pepsin. Also, the F(ab')2 can be produced by binding Fab' described below via a thioether bond or a disulfide bond.

The Fab' of the present invention can be obtained treating F(ab')2 which specifically reacts with hAMHR-II with a reducing agent, dithiothreitol. Also, the Fab' can be produced by inserting DNA encoding Fab' fragment of the antibody into an expression vector for prokaryote, or an expression vector for eukaryote, and introducing the vector into a prokaryote or eukaryote (as appropriate) to perform its expression.

The scFv of the present invention can be produced by obtaining cDNA encoding the VH and VL domains as previously described, constructing DNA encoding scFv, inserting the DNA into an expression vector for prokaryote, or an expression vector for eukaryote, and then introducing the expression vector into a prokaryote or eukaryote (as appropriate) to express the scFv. To generate a humanized scFv fragment, a well known technology called CDR grafting may be used, which involves selecting the complementary determining regions (CDRs) from a donor scFv fragment, and grafting them onto a human scFv fragment framework of known three dimensional structure (see, e.g., WO98/45322; WO 87/02671; U.S. Pat. No. 5,859,205; U.S. Pat. No. 5,585,089; U.S. Pat. No. 4,816,567; EP0173494).

Modification of the Antibodies of the Invention

Amino acid sequence modification(s) of the antibodies described herein are contemplated. For example, it may be desirable to improve the binding affinity and/or other biological properties of the antibody. It is known that when a humanized antibody is produced by simply grafting only CDRs in VH and VL of an antibody derived from a non-human animal in FRs of the VH and VL of a human antibody, the antigen binding activity is reduced in comparison with that of the original antibody derived from a non-human animal. It is considered that several amino acid residues of the VH and VL of the non-human antibody, not only in CDRs but also in FRs, are directly or indirectly associated with the antigen binding activity. Hence, substitution of these amino acid residues with different amino acid residues derived from FRs of the VH and VL of the human antibody would reduce of the binding activity. In order to resolve the problem, in antibodies grafted with human CDR, attempts have to be made to identify, among amino acid sequences of the FR of the VH and VL of human antibodies, an amino acid residue which is directly associated with binding to the antibody, or which interacts with an amino acid residue of CDR, or which maintains the three-dimensional structure of the antibody and which is directly associated with binding to the antigen. The reduced antigen binding activity could be increased by replacing the identified amino acids with amino acid residues of the original antibody derived from a non-human animal.

Modifications and changes may be made in the structure of the antibodies of the present invention, and in the DNA sequences encoding them, and still obtain a functional molecule that encodes an antibody and polypeptide with desirable characteristics.

The amino acid changes may be achieved by changing codons in the DNA sequence, according to Table 2.

TABLE 2

| Amino acids | | | Codons |
|---|---|---|---|
| Alanine | Ala | A | GCA, GCC, GCG, GCU |
| Cysteine | Cys | C | UGC, UGU |
| Aspartic Acid | Asp | D | GAC, GAU |
| Glutamic acid | Glu | E | GAA, GAG |
| Phenylalanine | Phe | F | UUC, UUU |
| Glycine | Gly | G | GGA, GGC, GGG, GGU |
| Histidine | His | H | CAC, CAU |
| Isoleucine | Ile | I | AUA, AUC, AUU |
| Lysine | Lys | K | AAA, AAG |
| Leucine | Leu | L | UUA, UUG, CUA, CUC, CUG, CUU |
| Methionine | Met | M | AUG |
| Asparagine | Asn | N | AAC, AAU |
| Proline | Pro | P | CCA, CCC, CCG, CCU |
| Glutamine | Gln | Q | CAA, CAG |
| Arginine | Arg | R | AGA, AGG, CGA, CGC, CGG, CGU |
| Serine | Ser | S | AGC, AGU, UCA, UCC, UCG, UCU |
| Threonine | Thr | T | ACA, ACC, ACG, ACU |
| Valine | Val | V | GUA, GUC, GUG, GUU |
| Tryptophan | Trp | W | UGG |
| Tyrosine | Tyr | Y | UAU |

In making the changes in the amino sequences of polypeptide, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (<RTI 3.5); asparagine (−3.5); lysine (−3.9); and arginine (−4.5).

A further object of the present invention also encompasses function-conservative variants of the antibodies of the present invention.

For example, certain amino acids may be substituted by other amino acids in a protein structure without appreciable loss of activity. Since the interactive capacity and nature of a protein define the protein's biological functional activity, certain amino acid substitutions can be made in a protein sequence, and, of course, in its DNA encoding sequence, while nevertheless obtaining a protein with like properties. It is thus contemplated that various changes may be made in the antibodies sequences of the invention, or corresponding DNA sequences which encode said polypeptides, without appreciable loss of their biological activity.

It is known in the art that certain amino acids may be substituted by other amino acids having a similar hydropathic index or score and still result in a protein with similar biological activity, i.e. still obtain a biological functionally equivalent protein.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

It may be also desirable to modify the antibody of the invention with respect to effector function, e.g. so as to enhance antigen-dependent cell-mediated cytotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing inter-chain disulfide bond formation in this region. The homodimeric antibody thus generated may have improved internalization capability and/or increased complement-mediated cell killing and/or antibody-dependent cellular cytotoxicity (ADCC) (Caron P C. et al. 1992; and Shopes B. 1992).

Another type of amino acid modification of the antibody of the invention may be useful for altering the original glycosylation pattern of the antibody.

By "altering" is meant deleting one or more carbohydrate moieties found in the antibody, and/or adding one or more glycosylation sites that are not present in the antibody.

Glycosylation of antibodies is typically N-linked. "N-linked" refers to the attachment of the carbohydrate moiety to the side chain of an asparagine residue. The tripeptide sequences asparagine-X-serine and asparagines-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites).

Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, orhydroxyproline, (e) aromatic residues such as those of phenylalanine, tyrosine, or tryptophan, or (f) the amide group of glutamine. For example, such methods are described in WO87/05330.

Removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Sojahr H. et al. (1987) and by Edge, A S. et al. (1981). Enzymatic cleavage of carbohydrate moieties on antibodies can be achieved by the use of a variety of endo- and exo-glycosidases as described by Thotakura, N R. et al. (1987).

Another type of covalent modification of the antibody comprises linking the antibody to one of a variety of non proteinaceous polymers, eg., polyethylene glycol, polypropylene glycol, or polyoxyalkylenes, in the manner set forth in U.S. Pat. No. 4,640,835; 4,496,689; 4,301,144; 4,670,417; 4,791,192 or 4,179,337.

Immunoconjugates

The invention relates to immunoconjugates comprising an antibody of the invention conjugated to an anti-cancer agent such as a cytotoxic agent or a growth inhibitory agent.

A "growth inhibitory agent" when used herein refers to a compound or composition which inhibits growth of a cell, especially ovarian cancer cell, either in vitro or in vivo. Examples of growth inhibitory agents include agents that block cell cycle progression, such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, and 5-fluorouracil. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $R^{186}$, $R^{188}$, $Sm^{153}$, $Bi^{212}$, $P^{32}$, and radioactive isotopes of Lu), chemotherapeutic agents, e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, e.g., gelonin, ricin, saporin, and the various antitumor or anticancer agents disclosed below. Other cytotoxic agents are described below. A tumoricidal agent causes destruction of tumor cells.

Conjugation of the antibodies of the invention with cytotoxic agents or growth inhibitory agents may be made using a variety of bifunctional protein coupling agents including but not limited to N-succinimidyl (2-pyridyldithio) propionate (SPDP), succinimidyl (N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6diisocyanate), and bis-active fluorine compounds (such as 1,5-difluoro-2,4-dinitrobenzene). For example, a ricin immunotoxin can be prepared as described in Vitetta et al (1987). Carbon labeled 1-isothiocyanatobenzyl methyldiethylene triaminepentaacetic acid (MX-DTPA) is an exemplary chelating agent for conjugation of radionucleotide to the antibody (WO 94/11026).

The linker may be a "cleavable linker" facilitating release of the cytotoxic agent or growth inhibitory agent in the cell. For example, an acid-labile linker, peptidase-sensitive linker, photolabile linker, dimethyl linker or disulfide-containing linker (See e.g. U.S. Pat. No. 5,208,020) may be used.

Alternatively, a fusion protein comprising the antibody and cytotoxic agent or growth inhibitory agent may be made, by recombinant techniques or peptide synthesis. The length of DNA may comprise respective regions encoding the two portions of the conjugate either adjacent one another or separated by a region encoding a linker peptide which does not destroy the desired properties of the conjugate.

The antibodies of the present invention may also be used in Dependent Enzyme Mediated Prodrug Therapy by conjugating the antibody to a prodrug-activating enzyme which converts a prodrug (e.g. a peptidyl chemotherapeutic agent, see WO81/01145) to an active anti-cancer drug (See, for example, WO 88/07378 and U.S. Pat. No. 4,975,278). The enzyme component of the immunoconjugate useful for ADEPT includes any enzyme capable of acting on a prodrug in such a way so as to covert it into its more active, cytotoxic form. Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic fluorocytosine into the anticancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as O-galactosidase and neuraminidase useful for converting glycosylated prodrugs into free drugs; β-lactamase useful for converting drugs derivatized with P-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. The enzymes can be covalently bound to the antibodies by techniques well known in the art such as the use of the heterobifunctional crosslinking reagents discussed above.

Diagnostic Methods and Uses

A further object of the invention relates to the use of an antibody of the invention for diagnosing and/or monitoring a cancer disease associated with AMHR-II expression. Cancer diseases associated with AMHR-II expression typically include ovarian cancers. In a preferred embodiment, antibodies of the invention are useful for diagnosing ovarian cancer including Granulosa cell tumours and epithelial ovarian cancers.

In a preferred embodiment, antibodies of the invention may be labelled with a detectable molecule or substance, such as a fluorescent molecule, a radioactive molecule or any others labels known in the art. Labels are known in the art that generally provide (either directly or indirectly) a signal.

As used herein, the term "labeled", with regard to the antibody, is intended to encompass direct labeling of the antibody by coupling (i.e., physically linking) a detectable substance, such as a radioactive agent or a fluorophore (e.g. fluorescein isothiocyanate (FITC) or phycoerythrin (PE) or Indocyanine (Cy5)) to the antibody, as well as indirect labeling of the antibody by reactivity with a detectable substance.

An antibody of the invention may be labelled with a radioactive molecule by any method known to the art. For example radioactive molecules include but are not limited radioactive atom for scintigraphic studies such as $I^{123}$, $I^{124}$, $In^{111}$, $Re^{186}$, $Re^{188}$. Antibodies of the invention may be also labelled with a spin label for nuclear magnetic resonance (NMR) imaging (also known as magnetic resonance imaging, mri), such as iodine-123, iodine-131, indium-I11, fluorine-19, carbon-13, nitrogen-15, oxygen-17, gadolinium, manganese or iron.

A "biological sample" encompasses a variety of sample types obtained from a subject and can be used in a diagnostic or monitoring assay. Biological samples include but are not limited to blood and other liquid samples of biological origin, solid tissue samples such as a biopsy specimen or tissue cultures or cells derived therefrom, and the progeny thereof. For example, biological samples include cells obtained from a tissue sample collected from an individual suspected of having a cancer disease associated with AMHR-II expression, and in a preferred embodiment from ovary. Therefore, biological samples encompass clinical samples, cells in culture, cell supernatants, cell lysates, serum, plasma, biological fluid, and tissue samples.

Antibodies of the invention may be useful for staging of cancer diseases associated with AMHR-II expression (e.g., in radioimaging). For example, antibodies of the invention may be useful for staging an ovarian cancer. They may be used alone or in combination with other ovarian cancer markers, including, but not limited to, CAl 25, HE4 and mesothelin.

The term "detection" as used herein includes qualitative and/or quantitative detection (measuring levels) with or without reference to a control.

In another aspect, the invention is a method of diagnosing a cancer disease associated with AMHR-II expression in a subject by detecting AMHR-II on cells from the subject using the antibody of the invention. In particular, said method of diagnosing may comprise the steps consisting of:

(a) contacting a biological sample of a subject likely to suffer from a cancer disease associated with AMHR-II expression with an antibody according to the invention in conditions sufficient for the antibody to form complexes with cells of the biological sample that express AMHR-II;

(b) detecting and/or quantifying said complexes, whereby the detection of said complexes is indicative of a cancer disease associated with AMHR-II expression.

In order to monitor the cancer disease, the method of diagnosing according to the invention may be repeated at different intervals of time, in order to determine if antibody binding to the samples increases or decreases, whereby it is determined if the cancer disease progresses or regresses.

Therapeutic Methods and Uses

Antibodies, fragments or immunoconjugates of the invention may be useful for treating any cancer disease associated with the expression of human AMHR-II. The antibodies of the invention may be used alone or in combination with any suitable agent.

It is well known that therapeutic monoclonal antibodies can lead to the depletion of cells bearing the antigen specifically recognized by the antibody. This depletion can be mediated through at least three mechanisms: antibody mediated cellular cytotoxicity (ADCC), complement dependent lysis, and direct anti-tumour inhibition of tumour growth through signals given via the antigen targeted by the antibody.

"Complement dependent cytotoxicity" or "CDC" refers to the lysis of a target cell in the presence of complement. Activation of the classical complement pathway is initiated by the binding of the first component of the complement system to antibodies which are bound to their cognate antigen. To assess complement activation, a CDC assay, e.g. as described in Gazzano-Santoro et al. (1997) may be performed.

"Antibody-dependent cell-mediated cytotoxicity" or "ADCC" refers to a form of cytotoxicity in which secreted antibodies bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell. To assess ADCC activity of a molecule of interest, an in vitro ADCC assay, such as that described in U.S. Pat. No. 5,500,362 or 5,821,337 may be performed.

In another embodiment antibodies of the invention may be conjugated to an growth inhibitory agent, cytotoxic agent, or a prodrug-activating enzyme as previously described. Antibodies of the invention may be indeed useful for targeting said growth inhibitory agent, cytotoxic agent, or a prodrug to the tumour cell expressing AMHR-II.

Thus, an object of the invention relates to a method for treating a cancer disease associated with the expression of AMHR-II comprising administering a subject in need thereof with a therapeutically effective amount of an antibody, fragment or immunoconjugate of the invention.

Cancer diseases associated with the expression of human AMHR-II typically include ovarian cancers. In a preferred embodiment, antibodies of the invention are useful for treating ovarian cancer including granulosa cell tumours and epithelial ovarian cancers.

In the context of the invention, the term "treating" or "treatment", as used herein, means reversing, alleviating, inhibiting the progress of, or preventing the disorder or condition to which such term applies, or one or more symptoms of such disorder or condition. By the term "treating ovarian cancer" as used herein is meant the inhibition of the growth of ovarian cancer cells. Preferably such treatment also leads to the regression of tumor growth, i.e., the decrease in size of a measurable tumor. Most preferably, such treatment leads to the complete regression of the tumor.

According to the invention, the term "patient" or "patient in need thereof" is intended for a human or non-human mammal affected or likely to be affected with an cancer disease with the expression of AMHR-II.

By a "therapeutically effective amount" of the polypeptide of the invention is meant a sufficient amount of the antibody to treat said cancer disease, at a reasonable benefit/risk ratio applicable to any medical treatment. It will be understood, however, that the total daily usage of the antibodies and compositions of the present invention will be decided by the attending physician within the scope of sound medical judgment. The specific therapeutically effective dose level for any particular patient will depend upon a variety of factors including the disorder being treated and the severity of the disorder; activity of the specific antibody employed; the specific composition employed, the age, body weight, general health, sex and diet of the patient; the time of administration, route of administration, and rate of excretion of the specific antibody employed; the duration of the treatment; drugs used in combination or coincidental with the specific polypeptide employed; and like factors well known in the medical arts. For example, it is well known within the skill of the art to start doses of the compound at levels lower than those required to achieve the desired therapeutic effect and to gradually increase the dosage until the desired effect is achieved.

Another object of the invention relates to the use of at least one antibody, fragment or immunoconjugate of the invention for the manufacture of a medicament intended for treating a cancer disease associated with expression of AMHR-II.

Antibodies of the invention may be used in combination with any other therapeutical strategy for treating ovarian cancer (e.g. external radiotherapy, chimiotherapy or cytokines).

Pharmaceutical Compositions

The polypeptide, nucleic acids or conjugates of the invention may be combined with pharmaceutically acceptable excipients, and optionally sustained-release matrices, such as biodegradable polymers, to form therapeutic compositions.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, parenteral, intranasal, intravenous, intramuscular, subcutaneous or intraocular administration and the like.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

To prepare pharmaceutical compositions, an effective amount of the antibody may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

An antibody of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The antibodies of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds formulated for parenteral administration, such as intravenous or intramuscular injection, other pharmaceutically acceptable forms include, e.g. tablets or other solids for oral administration; time release capsules; and any other form currently used.

In certain embodiments, the use of liposomes and/or nanoparticles is contemplated for the introduction of antibodies into host cells. The formation and use of liposomes and/or nanoparticles are known to those of skill in the art.

Nanocapsules can generally entrap compounds in a stable and reproducible way. To avoid side effects due to intracellular polymeric overloading, such ultrafine particles (sized around 0.1 μm) are generally designed using polymers able to be degraded in vivo. Biodegradable polyalkyl-cyanoacrylate nanoparticles that meet these requirements are contemplated for use in the present invention, and such particles may be are easily made.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 μm. Sonication of MLVs results in the formation of small unilamellar vesicles (SUVs) with diameters in the range of 200 to 500 Å, containing an aqueous solution in the core. The physical characteristics of liposomes depend on pH, ionic strength and the presence of divalent cations.

Kits

Finally, the invention also provides kits comprising at least one antibody of the invention. Kits containing antibodies of the invention find use in detecting AMHR-II expression, or in therapeutic or diagnostic assays. Kits of the invention can contain an antibody coupled to a solid support, e.g., a tissue culture plate or beads (e.g., sepharose beads). Kits can be provided which contain antibodies for detection and quantification of AMHR-II in vitro, e.g. in an ELISA or a Western blot. Such antibody useful for detection may be provided with a label such as a fluorescent or radiolabel.

The invention will further be illustrated in view of the following figures and examples.

FIGURES

FIG. 3 shows the nucleic acid sequence (SEQ ID NO: 11) and amino acid sequence (SEQ ID NO: 12) of the VH region of mAb 12G4.

EXAMPLE 1

Figure 1:
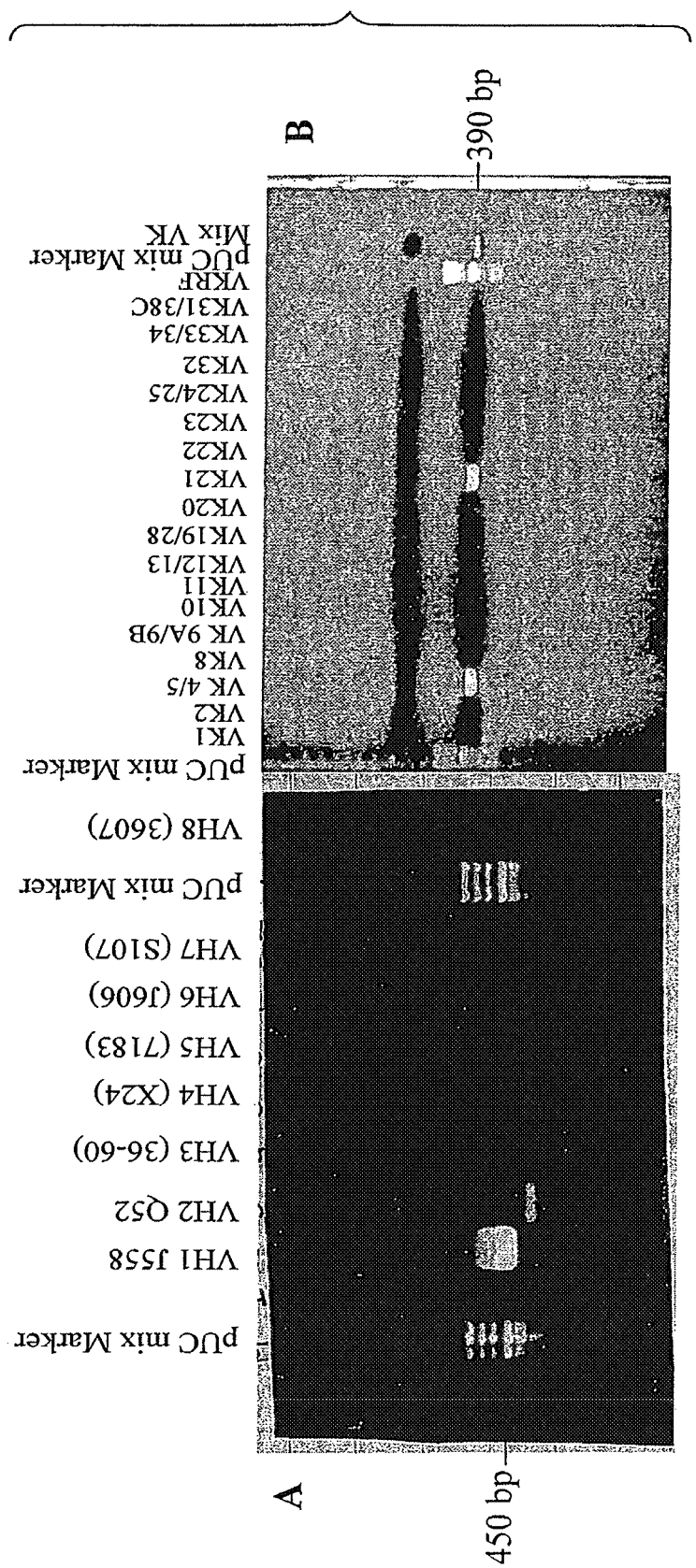
FIG. 1 shows the PCR amplification products for the (A) VH and (B) Vκ chain regions of mAb 12G4 using a combination of appropriate constant primer and signal primers corresponding to a given VH or Vκ gene family. Efficient sets of primers should amplify a 450 bp product for VH amplification and a 390 bp product for Vκ amplification.

A—Materials and Methods cDNA Synthesis and PCR Amplification of VH and Vκ Genes from Mouse Hybridoma:

Total RNA was extracted from 5×10$^6$ 12G4 hybridoma cells using the RNeasy Mini kit (Qiagen) as described by the manufacturer. After the extraction, a small fraction of the total RNA preparation was taken to determine the quality of the sample and the total RNA yield. Controls were performed by UV spectroscopy to verify RNA concentration and purity. Total RNA profile was analyzed using Agilent RNA 6000 Nano LabChipâ kit with the Agilent 2100 Bioanalyzer (Agilent Technologies, Palo Alto, Calif.) to determine its quantity and its integrity. cDNA synthesis was performed with 280 ng (1 µl) of total RNA using the Superscript First-strand synthesis system for RT-PCR (Invitrogen life Technologies) as described by the manufacturer. The first-cDNA synthesis reaction was primed using oligo (dT) to hybridize to 3' poly(A) tails. cDNA was kept at −20° C. until use.

PCR amplification was carried out in a final volume of 20 µl containing 1 µl of cDNA synthesis reaction, 10 µM dNTPs, 2 µl of 10×PCR buffer (New England Biolabs, Beverly, Mass., USA). Fourteen VH and 18 Vκ PCR reactions were set up using each group of family-specific 5' primers and the appropriate 3'-oligonucleotide probe matching the light or heavy chain constant region RevCκSalI and RevCγSalI primers, respectively. The primers that have been used are those described by Chardes et al. (1999) (see Tables 1 and 2 of the reference).

Two mixtures, containing all VH or Vκ 5' primers, were also set up. No PCR reaction was performed with primer specific for the VH13 (3609N) gene family since the only reported member assigned to this family is the non-functional allele of PC3609. The amount of each primer used was initially 10 µM. The reaction mixtures were heated to 94° C. for 5 min, then 2 U Vent DNA polymerase (New England Biolabs) was added and 30 cycles of amplification were carried out for 1 min at 94° C., 1 min at 55° C. and 2 min at 72° C. After a 10 min extension at 72° C., the PCR products were fractionated through a 1.5% agarose gel and stained with SYBR Green. Sets of 5' primers and 3' primers to a 390 bp product for Vκ amplification and a 450 bp product for VH amplification were selected from this family-specific PCR screening. Five replicates using the same selected primers were subjected to a new PCR as described above. The PCR-amplified DNA products were gel purified on a 1.5%, low melting temperature agarose gel (Gibco).

Direct Nucleotide Sequencing of the Amplified V Genes:

Direct sequencing was performed from 500 ng of each PCR product using the Value Read service for standard sequencing reactions of MWG Biotech (München, Germany).

B—Results

The sequences of the VH and VL regions of mAb 12G4 were determined using an efficient method of amplification and direct sequencing of mouse variable regions from any immunoglobulin gene family (Strohal et al. 1987). Briefly, murine V genes have been classified into 15 VH and 18 Vκ gene families, based upon amino acid and/or nucleotide sequence similarities. In an attempt to potentially amplify Immunoglobuline (Ig) genes from all V gene families, Strohal et al. have defined two original sets of leader primers which hybridize in the relatively conserved signal sequences of each heavy and light chain gene family. These primers have been routinely used in their laboratory to amplify and directly sequence the full-length variable regions from nine murine monoclonal antibodies (mAbs), including domains belonging to seven different Vκ and five different VH gene families. Their strategy allows rapid and accurate sequencing of variable regions from any Ig gene family and should facilitate the design of chimeric antibodies of clinical interest.

Total RNA Analysis:

Total RNA profile was analyzed using Agilent RNA 6000 Nano LabChipâ kit with the Agilent 2100 Bioanalyzer to determine its quantity and its integrity.

PCR Amplification of V Genes from Mouse Hybridoma 12G4 Using Gene Family-Specific Signal Primers:

FIG. 1 shows the PCR amplification products for the (A) VH and (B) Vκ chain regions of mAb 12G4 using a combination of appropriate constant primer and signal primers corresponding to a given VH or Vκ gene family. Efficient sets of primers should amplify a 450 bp product for VH amplification and a 390 bp product for Vκ amplification. From the cDNA of hybridoma cells secreting the anti-AMHR-II mAb 12G4 (IgG1/κ), major bands at the expected size were obtained (FIG. 1):

with the VH1-J558/RevCγSalI set of primers for heavy chain amplification. No amplification was obtained with primers VH9 (VGam 3-8), VH10, VH11, VH12, VH14 and VH15.

with the Vκ4/5/RevCκSalI or Vκ21/RevCκSalI set of primers for Vκ amplification.

Figure 2:
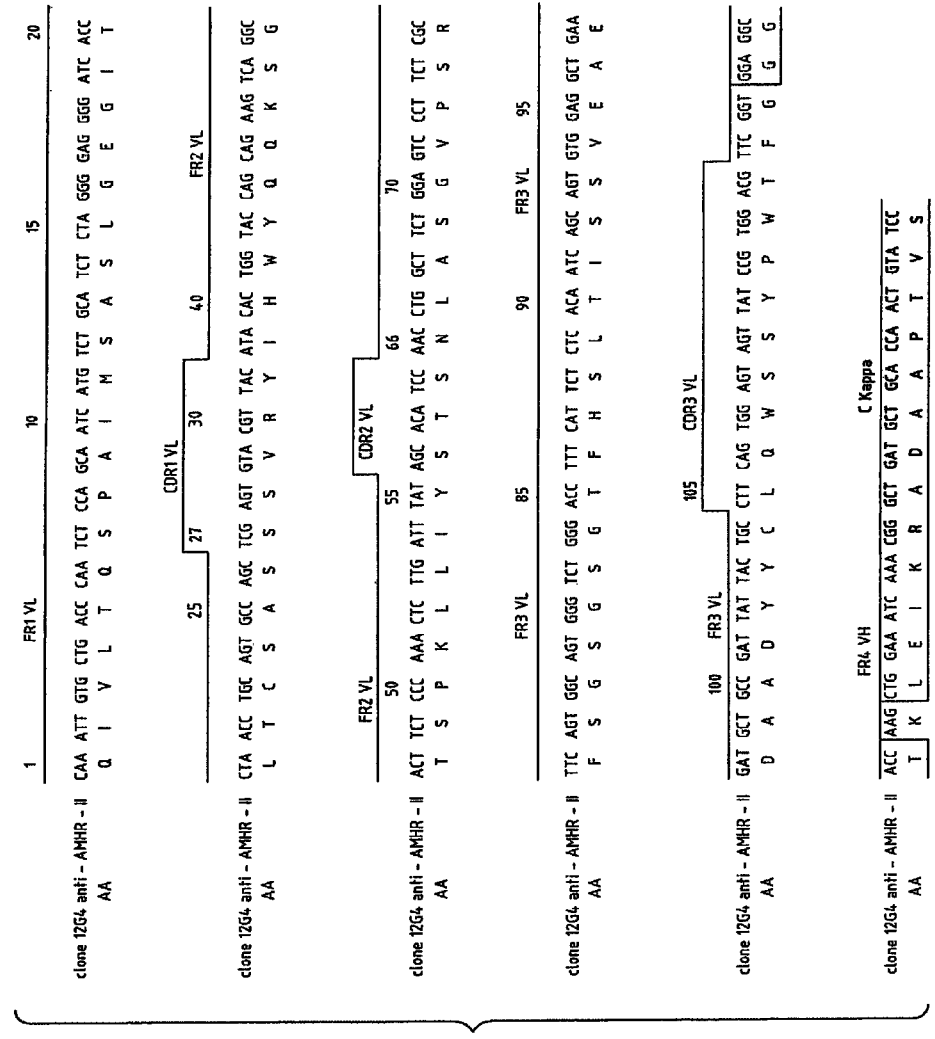
FIG. 2 shows the nucleic acid sequence (SEQ ID NO: 9) and amino acid sequence (SEQ ID NO: 10) of the VL region of mAb 12G4.

Gene Characterization of Variable Regions from mAb12G4 Following Direct Sequencing of the Amplification Products:

Further analysis of the assembled genes by direct sequencing of the amplification products showed that the VH gene belongs to a major VH gene family (VH1). The Vκ4/5 gene family was determined to be the gene family encoding Vκ 12G4 gene. The Vκ PCR product amplified with Vκ21 primers corresponds to a non-functionally rearranged kappa light chain transcribed in myeloma cell lines, like NS1, derived from the original MOPC21 tumour (Chardès et al. 1999). Inside each gene family, the closest germ line gene has been identified for the variable regions sequenced using the IMGT database. Sequences of the VL and VH regions are shown in FIGS. 2 and 3, respectively.

EXAMPLE 2

A—Material

Monoclonal Antibodies:
Anti-AMHR-II mAb 12G4:

The recombinant extra-cellular domain of human AMHR-II (ECD-hAMHR-II), expressed in bacteria and purified as an His-tag fusion protein (Gouedard L. et al., 2000), was used as immunogen. Mice hybridomas were generated by immunizing BALB/c mice four times i.p. at 3-week intervals with 20 μg of protein in complete Freund's adjuvant (Sigma) for the first injection, and incomplete Freund's adjuvant (Sigma) for subsequent injections. An i.v. booster injection of ECD-hAMHR-II was given three weeks after the fourth immunization. Three days later, spleen cells from immunized mice were fused with the mouse myeloma cell line P3-X63-Ag.8.653. Supernatants from newly generated clones were screened by ELISA using ECD-hAMHR-II. The specificity for hAMHR-II of supernatants was confirmed by fluorescence-activated cell sorting (FACs) on AMHR-II positive cells.

Anti-HER2MAbs:

Murine mAb FRP5 (Harweth I. et al., 1992) and humanized trastuzumab (Herceptin®) were used. Trastuzumab (Herceptin®) was purchased from Genentech, Inc. (San Francisco, Calif., USA).

MAbs Used as Controls:

In control experiments, anti-CEA monoclonal antibody 35A7 (specific for the CEA Gold 2 epitope, (Haskell C. et al. 1983; Hammarstrom S. et al., 1989) and PX (normal mouse IgG1 purified from the mouse myeloma P3-X63 (Köhler G. 1975)) were used as irrelevant antibodies. All the murine IgG1 MAbs were purified from mouse hybridoma ascites fluid by ammonium sulphate precipitation (45% saturation at 4° C.) followed by ion-exchange chromatography on. DE52 cellulose (Whatman, Balston, United Kingdom).

Cell Lines and Culture Conditions:

The human granulosa tumour cell line COV434 was kindly provided by the team of van den Berg-Bakker (van den Berg-Bakker C. et al., 1993). For obtaining the AMHR-II-positive transfected COV434-AMHR-II 1F3 cell line, we stably transfected the GCT tumour cell line COV434 with the encoding cDNA for human AMHR-II using the pIRES-EGFP vector (FuGENE 6 transfection kit, Roche Diagnostics) and then sub-cloned the COV434-AMHR-II 1F3 cell line.

All the cell lines were grown in DMEM F12 medium containing 10% heat-inactivated fetal bovine serum, streptomycin (0.1 mg/mL), penicillin (0.1 IU/mL) and amphotericin B (0.25 μg/mL). Cells were grown at 37° C. in a 5% CO2 atmosphere and medium was replaced twice a week. Harvest of the cells was done using trypsin (0.5 mg/mL) EDTA (0.2 mg/mL). All culture medium supplements were purchased from Life Technologies, Inc. (Gibco BRL, Gaithersburg, Md.). For the transfected cells, geneticine (0.67%) was added in the medium.

B—Methods and Results

Figure 4:
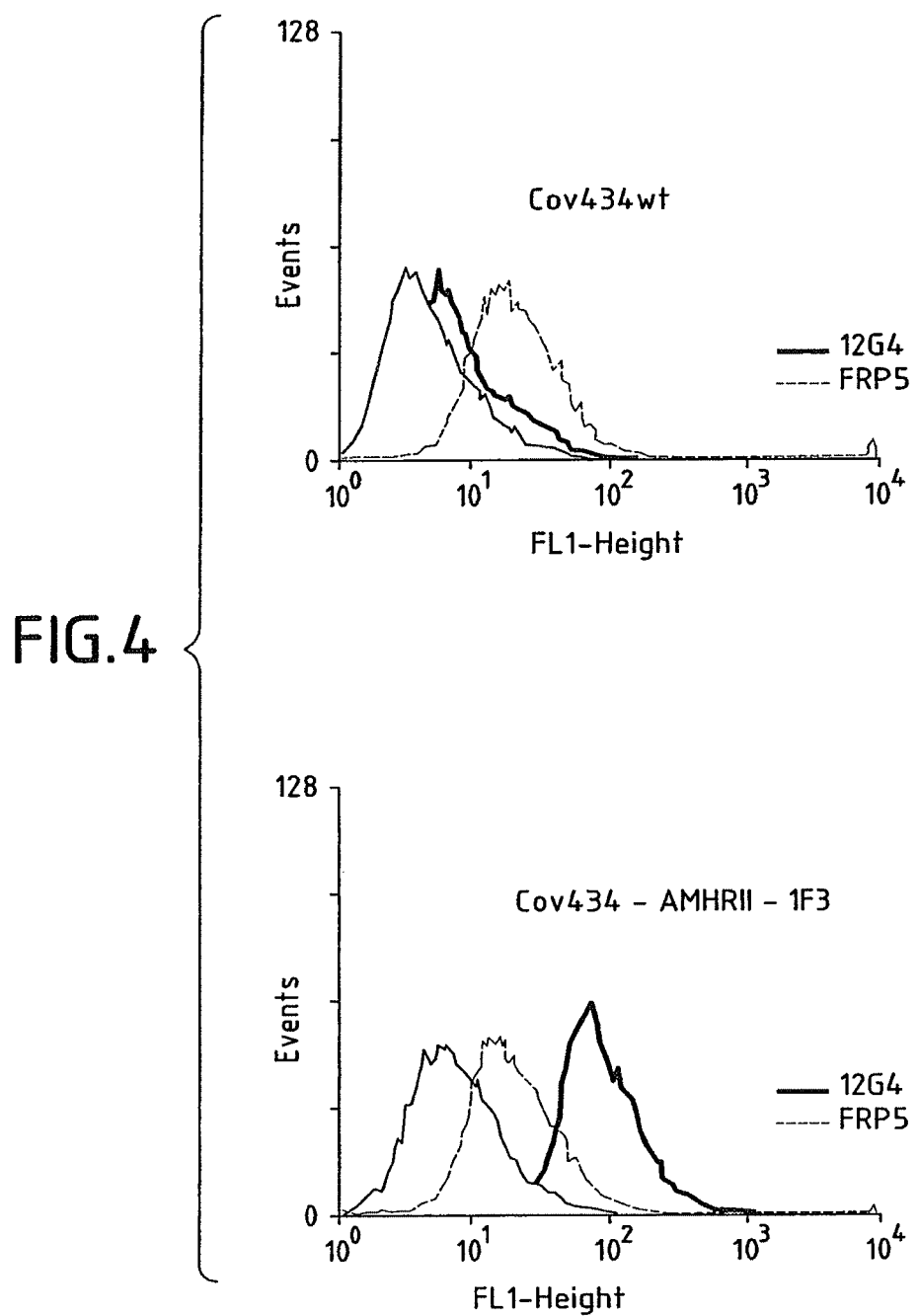
FIG. 4 shows the flow cytometry analysis of HER2 expression (grey line) and AMHR-II expression (black line) on the stably transfected COV434-pIRES-EGFP-AMHR-II 1F3 cell line.

Flow Cytometry Analysis of COV434-AMHR-II 1F3 Cell Line for the In Vitro and In Vivo Studies:

The COV434-AMHR-II 1F3 was analyzed by flow cytometry (FACs) using the murine anti-AMHR-II (12G4) and anti-HER2 (FRP5) antibodies, respectively. After washing, an anti-mouse FITC conjugated monoclonal antibody (Sigma Aldrich) was added to detect the primary antibodies. Direct incubation of cells with the secondary antibody was used for background measurements. The samples were analyzed on a FACScan II (Becton Dickinson, Mountain View, Calif., USA) by observing a minimum of 20000 events. The wild-type (wt) COV434 cell line was used as negative control (FIG. 4). By this technique, using the QIFIKIT (Dako, Danemark), we could evaluate an expression rate of about $10^4$ AMHR-II receptors/cell and $10^3$ HER2 receptors/cell.

Immunofluorescence Studies of the Internalization of mAb 12G4 in COV434-AMHR-II-1F3-Transfected Cell Line:

The ability of the antibodies to internalise in the COV434-AMHRII-1F3 cells was visualized using immunofluorescence. For each assay, $5 \cdot 10^4$ cells were grown with RPMI on a 22-mm square glass cover slip deposited in a 35-mm Petri dish. Two days later, during the logarithmic phase of growth, the cells were incubated with 10 μg/mL antibodies (either irrelevant mAb (PX), anti-AMHR-II (12G4), anti-HER2 (FRP5) or no antibody) on PBS-BSA (1 mg/mL) and placed at 4° C. (non-internalizing conditions) or transferred to a 37° C. incubator (internalising condition). At the 180 minutes, supernatants were removed, and the cells were washed twice with PBS-BSA and once with PBS. After a 20 minutes incubation in formalin (3.7% p-formaldehyde in PBS), the cells were permeabilized 30 seconds in acetone at −20° C. The solution was diluted successively by increasing the volume of PBS. The cells were washed twice with PBS-BSA and incubated for 1 h in the dark with an FITC-labelled goat anti-mouse Ig F(ab')2 fragment (Silenus, Eurobio, France) in PBS-BSA. Then they were washed three times with PBS-BSA and once with PBS and then incubated with 50 μl 4,6 diaminido-2-phenylindole dihydrochloride (DAPI, Sigma, Chemical Co.) for 15 minutes and prepared for fluorescent microscopic visualisation by Vectashield®.

It was demonstrated that anti-AMHR-II 12G4 and anti-HER2FRP5 antibodies could internalize in cells at 37° C. whereas PX does not. Indeed, fluorescent vesicles are clearly seen in the cytoplasm of cells. Therefore, MAbs were also incubated at 4° C. At this low temperature known to inhibit all active transport pathways, a much stronger labelling of the membrane was observed for both the specific antibodies, even at 4° C. None of these specific antibodies was found within the cells, despite the strong membrane association observed.

In Vitro Anti-Proliferative Effect of mAb12G4 (MTS Test):

The effect of trastuzumab, 12G4, FRP5 or 35A7 on cell viability was evaluated using a tetrazolium salt (MTS) and an electron coupling reagent (PMS) assay. Briefly, COV434-AMHR-II-1F3 cells were plated in 96-well microtiter plates at 5,000 cells/well in 100 µl of medium. After 24 h, the cells were treated with antibodies at concentrations ranging from 0.1 to 1 µg/µl. After incubation of 96 h, cells were exposed to MTS (3-(4,5-dimethylthiazol-2-yl)-5-(3-carboxymethoxyphenyl)-2-(4-sulfophenyl)-2H-tetrazolium) reagent and incubated at 37° C. for 2 h. Absorbance was measured at 490 nm, and the percent inhibition of viability was calculated as the percent of proliferating cells compared with untreated cultures. All experiments were performed in triplicate.

Figure 5:
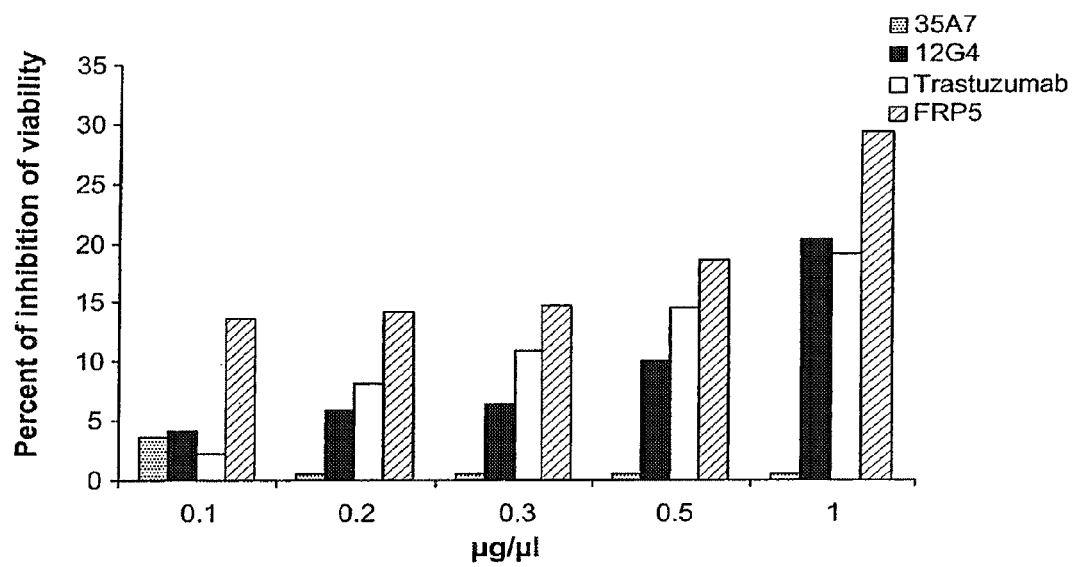
FIG. 5 shows the in vitro anti-proliferative effect on COV434-pIRES-EGFP-AMHR-II 1F3 cell line of mAb12G4, an aspecific mAb 35A7 and anti-HER2 trastuzumab and FRP5 mAbs measured by MTS test. A representative experiment of two is shown.

The results show that a percent inhibition of viability about 20% can be observed using either mAb 12G4 or trastuzumab at 1 µg/µl whereas at the same concentration no inhibition is observed with the anti-CEA 35A7 mAb (FIG. 5). The trastuzumab was used as positive control because its anti-proliferative effect has extensively been demonstrated.

Preliminary In Vivo Tumour Growth Inhibition Study:

All in vivo experiments were performed in compliance with the French guidelines for experimental animal studies (Agreement No. B34-172-27). Nude mice, 6-8-week-old female athymic nude mice were purchased from Harlan (Gannat, France).

COV434-AMHRII-1F3 (10·10$^6$) cells were suspended in 50% culture medium and 50% Matrigel (BD biosciences, Le Pont De Claix, France) and were injected subcutaneously (s.c.) into the right flank of athymic nude mice. Tumour-bearing mice were randomized in the different groups when the tumours reached approximately the same volume. The mice were treated by intra-peritoneal injections (i.p.) with 0.9% NaCl or mAb 12G4. The amounts of each injected mAb were 200 µg per injection, twice a week for five weeks consecutively.

Tumour dimensions were measured weekly with a caliper and the volumes calculated by the formula: D1×D2×D3/2.

Figure 6:
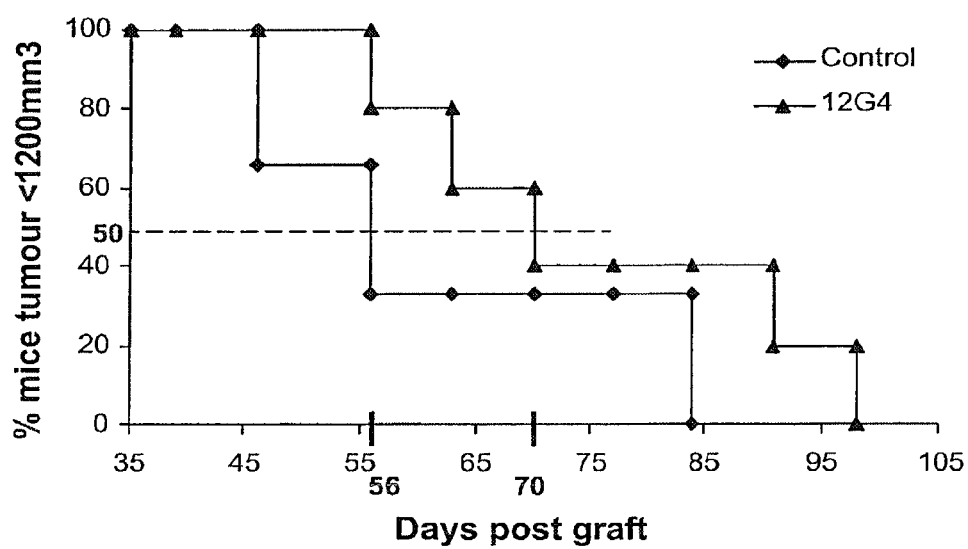
FIG. 6 shows a preliminary study of the in vivo effect of mAb 12G4 on the growth of COV434-AMHRII-1F3 xenografts in athymic nude mice. An adapted Kaplan-Meier curves using the time taken for the tumour to reach a determined volume of 1200 mm$^3$.

The results were expressed by an adapted Kaplan-Meier survival curve, using the time taken for the tumour to reach a determined volume of 1200 mm$^3$ (FIG. 6). A median delay was defined as the time at which 50% of the mice had a tumour reaching the determined volume and shows that this median delay is 14 days longer for the treated group as compared with the control NaCl group.

Immunoblotting Analysis of AMHR-II Expression in Xenografts:

Cells from xenografted tumours were rescued and lysed with RIPA buffer (50 mM Tris-HCl, pH 7.4, 150 mM NaCl, 1% deoxycholate, 1% NP40, 2 mM EDTA, 0.1% SDS and 1 mM phenylmethylsulfonyl fluoride). After electrophoresis on 10% SDS-PAGE under reducing conditions, the proteins were transferred to a polyvinylidene difluoride membranes (Millipore Co., Bedford, Mass.) which were saturated in PBS containing 5% non-fat dry milk and then incubated with the anti-AMHR-II 12G4 antibody.

Figure 7:
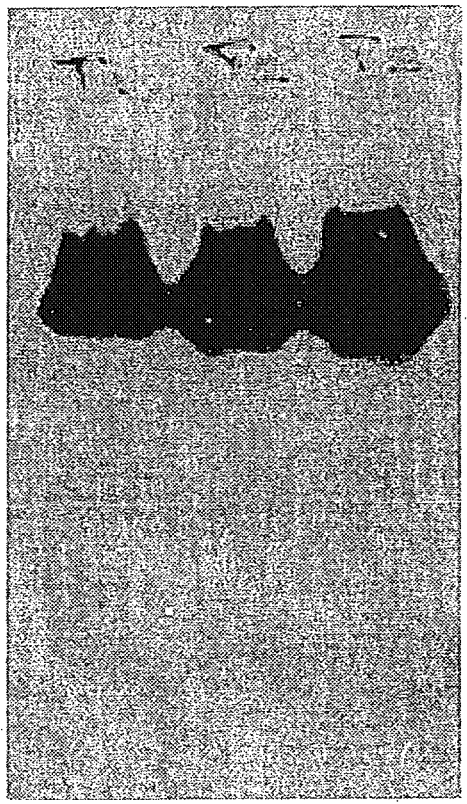
FIG. 7 shows the western blot analysis of AMHR-II expression in COV434-AMHRII-1F3 xenografts.

AMHR-II is strongly expressed in three different sections of the resected tumour and migrates at 65 kDa (FIG. 7).

REFERENCES

Baarends W M, Hoogerbrugge J W, Post M, Visser J A, De Rooij D G, Parvinen M, Themmen A P, Grootegoed J A Anti-mullerian hormone and anti-mullerian hormone type II receptor messenger ribonucleic acid expression during postnatal testis development and in the adult testis of the rat. Endocrinology. 1995 December; 136(12):5614-22.

Baarends W M, van Helmond M J, Post M, van der Schoot P J, Hoogerbrugge J W, de Winter J P, Uilenbroek J T, Karels B, Wilming L G, Meijers J H, et al. A novel member of the transmembrane serine/threonine kinase receptor family is specifically expressed in the gonads and in mesenchymal cells adjacent to the mullerian duct. Development. 1994 January; 120(1):189-97.

Behringer R R, Cate R L, Froelick G J, Palmiter R D, Brinster R L. Abnormal sexual development in transgenic mice chronically expressing mullerian inhibiting substance. Nature. 1990 May 10; 345(6271):167-70.

Belville C, Josso N, Picard J Y. Persistence of Mullerian derivatives in males. Am J Med Genet. 1999 Dec. 29; 89(4):218-23.

Berek J S, Taylor P T, Gordon A, Cunningham M J, Finkler N, Orr J Jr, Rivkin S, Schultes B C, Whiteside T L, Nicodemus C F. Randomized, placebo-controlled study of oregovomab for consolidation of clinical remission in patients with advanced ovarian cancer. J Clin Oncol. 2004 Sep. 1; 22(17):3507-16.

Black R J, Bray F, Ferlay J, Parkin D M. Cancer incidence and mortality in the European Union: cancer registry data and estimates of national incidence for 1990. Eur J. Cancer. 1997 June; 33(7):1075-107.

Brady G, Jantzen H M, Bernard H U, Brown R, Schutz G, Hashimoto-Gotoh T. New cosmid vectors developed for eukaryotic DNA cloning. Gene. 1984 February; 27(2): 223-32.

Caron P C, Laird W, Co M S, Avdalovic N M, Queen C, Scheinberg D A. Engineered humanized dimeric forms of IgG are more effective antibodies. J Exp Med. 1992 Oct. 1; 176(4):1191-5.

Chardes T, Villard S, Ferrieres G, Piechaczyk M, Cerutti M, Devauchelle G, Pau B. Efficient amplification and direct sequencing of mouse variable regions from any immunoglobulin gene family. FEBS Lett. 1999 Jun. 11; 452 (3):386-94.

Connolly D C, Bao R, Nikitin A Y, Stephens K C, Poole T W, Hua X, Harris S S, Vanderhyden B C, Hamilton T C. Female mice chimeric for expression of the simian virus 40 TAg under control of the MISIIR promoter develop epithelial ovarian cancer. Cancer Res. 2003 Mar. 15; 63(6):1389-97.

di Clemente N, Wilson C, Faure E, Boussin L, Carmillo P, Tizard R, Picard J Y, Vigier B, Josso N, Cate R. Cloning, expression, and alternative splicing of the receptor for anti-Mullerian hormone. Mol Endocrinol. 1994 August; 8(8):1006-20.

Dutertre M, Gouedard L, Xavier F, Long W Q, di Clemente N, Picard J Y, Rey R. Ovarian granulosa cell tumors express a functional membrane receptor for anti-Mullerian hormone in transgenic mice. Endocrinology. 2001 September; 142(9):4040-6.

Dutertre M, Rey R, Porteu A, Josso N, Picard J Y. A mouse Sertoli cell line expressing anti-Mullerian hormone and its type II receptor. Mol Cell Endocrinol. 1997 Dec. 31; 136(1):57-65.

Edge A S, Faltynek C R, H of L, Reichert L E Jr, Weber P. Deglycosylation of glycoproteins by trifluoromethanesulfonic acid. Anal Biochem. 1981 Nov. 15; 118(1):131-7.

Gazzano-Santoro H, Ralph P, Ryskamp T C, Chen A B, Mukku V R. A non-radioactive complement-dependent cytotoxicity assay for anti-CD20 monoclonal antibody. J Immunol Methods. 1997 Mar. 28; 202(2):163-71.

Gillies S D, Morrison S L, Oi V T, Tonegawa S. A tissue-specific transcription enhancer element is located in the major intron of a rearranged immunoglobulin heavy chain gene. Cell. 1983 July; 33(3):717-28.

Gordon A N, Schultes B C, Gallion H, Edwards R, Whiteside T L, Cermak J M, Nicodemus C F. CA125- and tumor-specific T-cell responses correlate with prolonged survival in oregovomab-treated recurrent ovarian cancer patients. Gynecol Oncol. 2004 August; 94(2):340-51.

Gouedard, L., Chen, Y. G., Thevenet, L., Racine, C., Borie, S., Lamarre, I., Josso, N., Massague, J., and di Clemente, N. (2000) J Biol Chem 275, 27973-27978.

Hammarstrom, S., Shively, J. E., Paxton, R. J., Beatty, B. G., Larson, A., Ghosh, R., Bormer, O., Buchegger, F., Mach, J.-P., Burtin, P., Seguin, P., Darbouret, B., Degorce, F., Sertour, J., Jolu, J.-P., Fuks, A., Kalthoff, H., Schmiegel, W., Arndt, R., Kloppel, G., von Kleist, S., Grunert, F., Schwarz, K., Matsuoka, Y., Kuroki, M., Wagener, C., Weber, T., Yachi, A., Imai, K., Hishikawa, N., and Tsujisaki, M. (1989) Cancer Res 49, 4852-4858.

Harwerth, I. M., Wels, W., Marte, B. M., and Hynes, N. E. (1992) J. Biol. Chem. 267, 15160-15167.

Haskell, C. M., Buchegger, F., Schreyer, M., Carrel, S., and Mach, J.-P. (1983) Cancer Res 43, 3857-3864.

Imbeaud S, Faure E, Lamarre I, Mattei M G, di Clemente N, Tizard R, Carre-Eusebe D, Belville C, Tragethon L, Tonkin C, Nelson J, McAuliffe M, Bidart J M, Lababidi A, Josso N, Cate R L, Picard J Y. Insensitivity to anti-mullerian hormone due to a mutation in the human anti-mullerian hormone receptor. Nat. Genet. 1995 December; 11(4):382-8.

Köhler G., M. C. (1975) Nature 256, 495-497.

Kuwana Y, Asakura Y, Utsunomiya N, Nakanishi M, Arata Y, Itoh S, Nagase F, Kurosawa Y. Expression of chimeric receptor composed of immunoglobulin-derived V regions and T-cell receptor-derived C regions. Biochem Biophys Res Commun. 1987 Dec. 31; 149(3):960-8.

Lee M M, Seah C C, Masiakos P T, Sottas C M, Preffer F I, Donahoe P K, Maclaughlin D T, Hardy M P. Mullerian-inhibiting substance type II receptor expression and function in purified rat Leydig cells. Endocrinology. 1999 June; 140(6):2819-27.

Masiakos P T, MacLaughlin D T, Maheswaran S, Teixeira J, Fuller A F Jr, Shah P C, Kehas D J, Kenneally M K, Dombkowski D M, Ha T U, Preffer F I, Donahoe P K. Human ovarian cancer, cell lines, and primary ascites cells express the human Mullerian inhibiting substance (MIS) type II receptor, bind, and are responsive to MIS. Clin Cancer Res. 1999 November; 5(11):3488-99.

Mason J O, Williams G T, Neuberger M S. Transcription cell type specificity is conferred by an immunoglobulin V H gene promoter that includes a functional consensus sequence. Cell. 1985 June; 41(2):479-87.

Miyaji H, Mizukami T, Hosoi S, Sato S, Fujiyoshi N, Itoh S. Expression of human beta-interferon in Namalwa KJM-1 which was adapted to serum-free medium. Cytotechnology. 1990 March; 3(2):133-40.

Mizukami T, Itoh S. A new SV40-based vector developed for cDNA expression in animal cells. J Biochem (Tokyo). 1987 May; 101(5):1307-10.

Morrison S L, Johnson M J, Herzenberg L A, Oi V T. Chimeric human antibody molecules: mouse antigen-binding domains with human constant region domains. Proc Natl Acad Sci USA. 1984 November; 81(21):6851-5.

Neuberger M S, Williams G T, Fox R O. Recombinant antibodies possessing novel effector functions. Nature. 1984 Dec. 13-19; 312(5995):604-8.

O'Hare K, Benoist C, Breathnach R. Transformation of mouse fibroblasts to methotrexate resistance by a recombinant plasmid expressing a prokaryotic dihydrofolate reductase. Proc Natl Acad Sci USA. 1981 March; 78(3): 1527-31.

Ozols R F, Bookman M A, Connolly D C, Daly M B, Godwin A K, Schilder R J, Xu X, Hamilton T C. Focus on epithelial ovarian cancer. Cancer Cell. 2004 January; 5(1):19-24.

Padlan E A. A possible procedure for reducing the immunogenicity of antibody variable domains while preserving their ligand-binding properties. Mol. Immunol. 1991 April-May; 28(4-5):489-98.

Racine C, Rey R, Forest M G, Louis F, Ferre A, Huhtaniemi I, Josso N, di Clemente N. Receptors for anti-mullerian hormone on Leydig cells are responsible for its effects on steroidogenesis and cell differentiation. Proc Natl Acad Sci USA. 1998 Jan. 20; 95(2):594-9.

Rapkiewicz A V, Espina V, Petricoin E F 3rd, Liotta L A. Biomarkers of ovarian tumours. Eur J. Cancer. 2004 November; 40(17):2604-12.

Riechmann L, Clark M, Waldmann H, Winter G Reshaping human antibodies for therapy. Nature. 1988 Mar. 24; 332(6162):323-7.

Roguska M A, Pedersen J T, Keddy C A, Henry A H, Searle S J, Lambert J M, Goldmacher V S, Blattler W A, Rees A R, Guild B C. Humanization of murine monoclonal antibodies through variable domain resurfacing. Proc Natl Acad Sci USA. 1994 Feb. 1; 91(3):969-73.

Salhi I, Cambon-Roques S, Lamarre I, Laune D, Molina F, Pugniere M, Pourquier D, Gutowski M, Picard J Y, Xavier F, Pelegrin A, Navarro-Teulon I. The anti-Mullerian hormone type II receptor: insights into the binding domains recognized by a monoclonal antibody and the natural ligand. Biochem J. 2004 May 1; 379(Pt 3):785-93.

Segev D L, Ha T U, Tran T T, Kenneally M, Harkin P, Jung M, MacLaughlin D T, Donahoe P K, Maheswaran S. Mullerian inhibiting substance inhibits breast cancer cell growth through an NFkappa B-mediated pathway. J Biol. Chem. 2000 Sep. 15; 275(37):28371-9.

Segev D L, Hoshiya Y, Hoshiya M, Tran T T, Carey J L, Stephen A E, MacLaughlin D T, Donahoe P K, Maheswaran S. Mullerian-inhibiting substance regulates N F-kappa B signaling in the prostate in vitro and in vivo. Proc Natl Acad Sci USA. 2002 Jan. 8; 99(1):239-44. Epub 2002 Jan. 2.

Shitara K, Nakamura K, Tokutake-Tanaka Y, Fukushima M, Hanai N. A new vector for the high level expression of chimeric antibodies in myeloma cells. J Immunol Methods. 1994 Jan. 3; 167(1-2):271-8.

Shopes B. A genetically engineered human IgG mutant with enhanced cytolytic activity. J. Immunol. 1992 May 1; 148(9):2918-22.

Singh-Ranger G, Sharp A, Crinnion J N. Recurrence of granulosa cell tumour after thirty years with small bowel obstruction. Int Semin Surg Oncol. 2004 May 11; 1(1):4.

Strohal R, Kroemer G, Wick G, Kofler R. Complete variable region sequence of a nonfunctionally rearranged kappa light chain transcribed in the nonsecretor P3-X63-Ag8.653 myeloma cell line. Nucleic Acids Res. 1987 Mar. 25; 15(6):2771.

Studnicka G M, Soares S, Better M, Williams R E, Nadell R, Horwitz A H. Human-engineered monoclonal antibodies retain full specific binding activity by preserving non-CDR complementarity-modulating residues. Protein Eng. 1994 June; 7(6):805-14.

Teixeira J, Donahoe P K. Molecular biology of MIS and its receptors. J Androl. 1996 July-August; 17(4):336-41.

Thotakura N R, Bahl O P. Enzymatic deglycosylation of glycoproteins. Methods Enzymol. 1987; 138:350-9.

Tsuji M, Shima H, Yonemura C Y, Brody J, Donahoe P K, Cunha G R. Effect of human recombinant mullerian inhibiting substance on isolated epithelial and mesenchymal cells during mullerian duct regression in the rat. Endocrinology. 1992 September; 131(3):1481-8.

Urlaub G, Chasin L A. Isolation of Chinese hamster cell mutants deficient in dihydrofolate reductase activity. Proc Natl Acad Sci USA. 1980 July; 77(7):4216-20.

van den Berg-Bakker, C. A., Hagemeijer, A., Franken-Postma, E. M., Smit, V. T., Kuppen, P. J., van Ravenswaay Claasen, H. H., Cornelisse, C. J., and Schrier, P. I. (1993) Int J Cancer 53, 613-620.

Vitetta E S, Fulton R J, May R D, Till M, Uhr J W. Redesigning nature's poisons to create anti-tumor reagents. Science. 1987 Nov. 20; 238(4830):1098-104.

Yahata H, Kobayashi H, Kamura T, Amada S, Hirakawa T, Kohno K, Kuwano M, Nakano H. Increased nuclear localization of transcription factor YB-1 in acquired cisplatin-resistant ovarian cancer. J Cancer Res Clin Oncol. 2002 November; 128(11):621-6. Epub 2002 Oct. 22.

Yuan Q A, Simmons H H, Robinson M K, Russeva M, Marasco W A, Adams G P. Development of engineered antibodies specific for the Mullerian inhibiting substance type II receptor: a promising candidate for targeted therapy of ovarian cancer. Mol Cancer Ther. 2006 August; 5(8):2096-105.

Zhang H, Vollmer M, De Geyter M, Litzistorf Y, Ladewig A, Durrenberger M, Guggenheim R, Miny P, Holzgreve W, De Geyter C. Characterization of an immortalized human granulosa cell line (COV434). Mol Hum Reprod. 2000 February; 6(2):146-53.

What is claimed is:

1. An isolated immunoglobulin heavy and/or light chain having specificity for human Anti-Müllerian Hormone type II receptor (AMHR-II), wherein said heavy and/or light chain comprises a variable domain having the amino acid sequence set forth as SEQ ID NO:1 or SEQ ID NO:5.

2. The immunoglobulin chain according to claim 1, which is a heavy chain.

3. The immunoglobulin chain according to claim 1, which is a light chain.

4. An isolated monoclonal antibody having specificity for human Anti-Müllerian Hormone type II receptor (AMHR-II) which comprises:

(a) a heavy chain wherein the variable domain comprises SEQ ID NO:2 for CDR-1, SEQ ID NO:3 for CDR-2 and SEQ ID NO:4 for CDR-3; and (b) a light chain wherein the variable domain comprises: CDR-1 comprising SEQ ID NO:6, CDR-3 comprising SEQ ID NO:8 and CDR-2 comprising SEQ ID NO:7 or a variant thereof that differs by one amino acid residue.

5. The monoclonal antibody according to claim 4, wherein said antibody is a murine antibody.

6. The monoclonal antibody according to claim 4, wherein said antibody is a mouse/human chimeric antibody.

7. The monoclonal antibody according to claim 4, wherein said antibody is an humanized antibody.

8. An isolated fragment of a monoclonal antibody according to claim 4.

9. The fragment according to claim 8, selected in the group consisting of Fv, Fab, F(ab')2, Fab', dsFv, scFv, sc(Fv)2 and diabodies fragments.

10. A pharmaceutical composition comprising an isolated fragment according to claim 8 together with a pharmaceutically acceptable carrier.

11. An immunoconjugate comprising a fragment according to claim 8, conjugated to an anti-cancer agent.

12. The immunoconjugate according to claim 11 wherein said anti-cancer agent is a cytotoxic agent or a growth inhibitory agent.

13. The fragment according to claim 8, which is labelled with a detectable molecule or substance.

14. A pharmaceutical composition comprising an isolated antibody according to claim 4 together with a pharmaceutically acceptable carrier.

15. An immunoconjugate comprising an antibody according to claim 4, conjugated to an anti-cancer agent.

16. The immunoconjugate according to claim 15 wherein said anti-cancer agent is a cytotoxic agent or a growth inhibitory agent.

17. The antibody according to claim 4, which is labelled with a detectable molecule or substance.

18. A method for treating an ovarian cancer comprising administering a subject in need thereof with a therapeutically effective amount of an isolated antibody, or an isolated fragment of an antibody, or an isolated immunoconjugate comprising an antibody or a fragment of an antibody conjugated to an anticancer agent,
wherein the antibody is specific for human Anti-Müllerian Hormone type II receptor (AMHR-II) and comprises:
 (a) a heavy chain wherein the variable domain comprises SEQ ID NO: 2 for CDR-1, SEQ ID NO: 3 for CDR-2 and SEQ ID No: 4 for CDR-3; and
 (b) a light chain wherein the variable domain comprises: CDR-1 comprising SEQ ID NO:6, CDR-3 comprising SEQ ID NO:8 and CDR-2 comprising SEQ ID NO:7 or a variant thereof that differs by one amino acid residue.

19. A method of diagnosing and/or monitoring an ovarian cancer in a subject, comprising the steps of:
 (i) contacting a biological sample of a subject likely to suffer from an ovarian cancer with an isolated antibody, or an isolated fragment of an antibody, wherein the antibody is specific for human Anti-Müllerian Hormone type II receptor (AMHR-II) and comprises:
  (a) a heavy chain wherein the variable domain comprises SEQ ID NO: 2 for CDR-1, SEQ ID NO: 3 for CDR-2 and SEQ ID No: 4 for CDR-3; and
  (b) a light chain wherein the variable domain comprises: CDR-1 comprising SEQ ID NO:6, CDR-3 comprising SEQ ID NO:8 and CDR-2 comprising SEQ ID NO:7 or a variant thereof that differs by one amino acid residue,
 in conditions sufficient for the antibody or the fragment of antibody to form complexes with cells of the biological sample that express AMHR-II and
 (ii) detecting and/or quantifying said complexes;
whereby the detection of said complexes is indicative of an ovarian cancer.

* * * * *

SEQUENCE LISTING

```
<160> NUMBER OF SEQ ID NOS: 12

<210> SEQ ID NO 1
<211> LENGTH: 115
<212> TYPE: PRT
<213> ORGANISM: Mus musculus

<400> SEQUENCE: 1

Gln Val Gln Leu Gln Gln Ser Gly Pro Glu Leu Val Lys Pro Gly Ala
1               5                   10                  15

Ser Val Arg Met Ser Cys Lys Ala Ser Gly Tyr Thr Phe Thr Ser Tyr
            20                  25                  30

His Ile His Trp Val Lys Gln Arg Pro Gly Gln Gly Leu Glu Trp Ile
        35                  40                  45

Gly Trp Ile Tyr Pro Gly Asp Asp Ser Thr Lys Tyr Asn Glu Lys Phe
    50                  55                  60

Lys Gly Lys Thr Thr Leu Thr Ala Asp Lys Ser Ser Ser Thr Ala Tyr
65                  70                  75                  80

Met Leu Leu Ser Ser Leu Thr Ser Glu Asp Ser Ala Ile Tyr Phe Cys
                85                  90                  95

Thr Arg Gly Asp Arg Phe Ala Tyr Trp Gly Gln Gly Thr Leu Val Thr
            100                 105                 110

Val Ser Ala
        115

<210> SEQ ID NO 2
<211> LENGTH: 8
<212> TYPE: PRT
<213> ORGANISM: Mus musculus

<400> SEQUENCE: 2

Gly Tyr Thr Phe Thr Ser Tyr His
1               5

<210> SEQ ID NO 3
<211> LENGTH: 8
<212> TYPE: PRT
<213> ORGANISM: Mus musculus

<400> SEQUENCE: 3

Ile Tyr Pro Gly Asp Asp Ser Thr
1               5
```

<210> SEQ ID NO 4
<211> LENGTH: 8
<212> TYPE: PRT
<213> ORGANISM: Mus musculus

<400> SEQUENCE: 4

Thr Arg Gly Asp Arg Phe Ala Tyr
1               5

<210> SEQ ID NO 5
<211> LENGTH: 105
<212> TYPE: PRT
<213> ORGANISM: Mus musculus

<400> SEQUENCE: 5

Gln Ile Val Leu Thr Gln Ser Pro Ala Ile Met Ser Ala Ser Leu Gly
1               5                   10                  15

Glu Gly Ile Thr Leu Thr Ser Cys Ala Ser Ser Val Arg Tyr Ile
                20                  25                  30

His Trp Tyr Gln Gln Lys Ser Gly Thr Ser Pro Lys Leu Leu Ile Tyr
            35                  40                  45

Ser Thr Ser Asn Leu Ala Ser Gly Val Pro Ser Arg Phe Ser Gly Ser
        50                  55                  60

Gly Ser Gly Thr Phe His Ser Leu Thr Ile Ser Ser Val Glu Ala Glu
65                  70                  75                  80

Asp Ala Ala Tyr Tyr Cys Leu Gln Trp Ser Ser Tyr Pro Trp Thr Phe
                85                  90                  95

Gly Gly Gly Thr Lys Leu Glu Ile Lys
            100                 105

<210> SEQ ID NO 6
<211> LENGTH: 5
<212> TYPE: PRT
<213> ORGANISM: Mus musculus

<400> SEQUENCE: 6

Ser Ser Val Arg Tyr
1               5

<210> SEQ ID NO 7
<211> LENGTH: 3
<212> TYPE: PRT
<213> ORGANISM: Mus musculus

<400> SEQUENCE: 7

Ser Thr Ser
1

<210> SEQ ID NO 8
<211> LENGTH: 9
<212> TYPE: PRT
<213> ORGANISM: Mus musculus

<400> SEQUENCE: 8

Leu Gln Trp Ser Ser Tyr Pro Trp Thr
1               5

<210> SEQ ID NO 9
<211> LENGTH: 345
<212> TYPE: DNA
<213> ORGANISM: Mus musculus

<220> FEATURE:
<221> NAME/KEY: CDS
<222> LOCATION: (1)..(345)

<400> SEQUENCE: 9

```
caa att gtg ctg acc caa tct cca gca atc atg tct gca tct cta ggg      48
Gln Ile Val Leu Thr Gln Ser Pro Ala Ile Met Ser Ala Ser Leu Gly
1               5                   10                  15 gag ggg atc acc cta acc tgc agt gcc agc tcg agt gta cgt tac ata      96
Glu Gly Ile Thr Leu Thr Cys Ser Ala Ser Ser Ser Val Arg Tyr Ile
            20                  25                  30 cac tgg tac cag cag aag tca ggc act tct ccc aaa ctc ttg att tat     144
His Trp Tyr Gln Gln Lys Ser Gly Thr Ser Pro Lys Leu Leu Ile Tyr
        35                  40                  45 agc aca tcc aac ctg gct tct gga gtc cct tct cgc ttc agt ggc agt     192
Ser Thr Ser Asn Leu Ala Ser Gly Val Pro Ser Arg Phe Ser Gly Ser
    50                  55                  60 ggg tct ggg acc ttt cat tct ctc aca atc agc agt gtg gag gct gaa     240
Gly Ser Gly Thr Phe His Ser Leu Thr Ile Ser Ser Val Glu Ala Glu
65                  70                  75                  80 gat gct gcc gat tat tac tgc ctt cag tgg agt agt tat ccg tgg acg     288
Asp Ala Ala Asp Tyr Tyr Cys Leu Gln Trp Ser Ser Tyr Pro Trp Thr
                85                  90                  95 ttc ggt gga ggc acc aag ctg gaa atc aaa cgg gct gat gct gca cca     336
Phe Gly Gly Gly Thr Lys Leu Glu Ile Lys Arg Ala Asp Ala Ala Pro
            100                 105                 110 act gta tcc                                                         345
Thr Val Ser
        115
```

<210> SEQ ID NO 10
<211> LENGTH: 115
<212> TYPE: PRT
<213> ORGANISM: Mus musculus

<400> SEQUENCE: 10

```
Gln Ile Val Leu Thr Gln Ser Pro Ala Ile Met Ser Ala Ser Leu Gly
1               5                   10                  15

Glu Gly Ile Thr Leu Thr Cys Ser Ala Ser Ser Ser Val Arg Tyr Ile
            20                  25                  30

His Trp Tyr Gln Gln Lys Ser Gly Thr Ser Pro Lys Leu Leu Ile Tyr
        35                  40                  45

Ser Thr Ser Asn Leu Ala Ser Gly Val Pro Ser Arg Phe Ser Gly Ser
    50                  55                  60

Gly Ser Gly Thr Phe His Ser Leu Thr Ile Ser Ser Val Glu Ala Glu
65                  70                  75                  80

Asp Ala Ala Asp Tyr Tyr Cys Leu Gln Trp Ser Ser Tyr Pro Trp Thr
                85                  90                  95

Phe Gly Gly Gly Thr Lys Leu Glu Ile Lys Arg Ala Asp Ala Ala Pro
            100                 105                 110

Thr Val Ser
        115
```

<210> SEQ ID NO 11
<211> LENGTH: 360
<212> TYPE: DNA
<213> ORGANISM: Mus musculus
<220> FEATURE:
<221> NAME/KEY: CDS
<222> LOCATION: (1)..(360)

```
<400> SEQUENCE: 11 cag gtc cag ctg cag cag tct gga cct gaa ctg gtg aag cct ggg gct      48
Gln Val Gln Leu Gln Gln Ser Gly Pro Glu Leu Val Lys Pro Gly Ala
1               5                   10                  15 tca gtg agg atg tcc tgc aag gct tct ggc tac acc ttc aca agt tac      96
Ser Val Arg Met Ser Cys Lys Ala Ser Gly Tyr Thr Phe Thr Ser Tyr
            20                  25                  30 cat ata cac tgg gtg aag cag agg cct gga cag gga ctt gag tgg att     144
His Ile His Trp Val Lys Gln Arg Pro Gly Gln Gly Leu Glu Trp Ile
        35                  40                  45 gga tgg att tat cct ggc gat gat tct act aaa tac aat gag aag ttc     192
Gly Trp Ile Tyr Pro Gly Asp Asp Ser Thr Lys Tyr Asn Glu Lys Phe
    50                  55                  60 aag ggc aag acc aca ctg act gca gac aaa tcc tcc agc aca gcc tac     240
Lys Gly Lys Thr Thr Leu Thr Ala Asp Lys Ser Ser Ser Thr Ala Tyr
65                  70                  75                  80 atg ttg ctc agc agc ctg acc tct gag gac tct gcg atc tat ttc tgt     288
Met Leu Leu Ser Ser Leu Thr Ser Glu Asp Ser Ala Ile Tyr Phe Cys
                85                  90                  95 aca agg ggg gac cgc ttt gct tac tgg ggc caa ggg act ctg gtc act     336
Thr Arg Gly Asp Arg Phe Ala Tyr Trp Gly Gln Gly Thr Leu Val Thr
            100                 105                 110 gtc tct gca gcc aaa acg aca ccc                                     360
Val Ser Ala Ala Lys Thr Thr Pro
        115                 120

<210> SEQ ID NO 12
<211> LENGTH: 120
<212> TYPE: PRT
<213> ORGANISM: Mus musculus

<400> SEQUENCE: 12

Gln Val Gln Leu Gln Gln Ser Gly Pro Glu Leu Val Lys Pro Gly Ala
1               5                   10                  15

Ser Val Arg Met Ser Cys Lys Ala Ser Gly Tyr Thr Phe Thr Ser Tyr
            20                  25                  30

His Ile His Trp Val Lys Gln Arg Pro Gly Gln Gly Leu Glu Trp Ile
        35                  40                  45

Gly Trp Ile Tyr Pro Gly Asp Asp Ser Thr Lys Tyr Asn Glu Lys Phe
    50                  55                  60

Lys Gly Lys Thr Thr Leu Thr Ala Asp Lys Ser Ser Ser Thr Ala Tyr
65                  70                  75                  80

Met Leu Leu Ser Ser Leu Thr Ser Glu Asp Ser Ala Ile Tyr Phe Cys
                85                  90                  95

Thr Arg Gly Asp Arg Phe Ala Tyr Trp Gly Gln Gly Thr Leu Val Thr
            100                 105                 110

Val Ser Ala Ala Lys Thr Thr Pro
        115                 120
```